United States Patent
Corey et al.

(10) Patent No.: US 7,523,649 B2
(45) Date of Patent: Apr. 28, 2009

(54) METHOD AND APPARATUS FOR ULTRASONIC DETERMINATION OF HEMATOCRIT AND HEMOGLOBIN CONCENTRATIONS

(75) Inventors: Francis Scott Corey, Hydes, MD (US); Ben Lane, Phoenix, MD (US); Brian Murphy, Baltimore, MD (US); Brian Lipford, Belair, MD (US); Samuel Reed, North Garden, VA (US)

(73) Assignee: Separation Technology, Inc., Altomonte Springs, FL (US)

( * ) Notice: Subject to any disclaimer, the term of this patent is extended or adjusted under 35 U.S.C. 154(b) by 49 days.

(21) Appl. No.: 10/580,697

(22) PCT Filed: Nov. 26, 2004

(86) PCT No.: PCT/US2004/039735

§ 371 (c)(1),
(2), (4) Date: Apr. 17, 2007

(87) PCT Pub. No.: WO2005/054811

PCT Pub. Date: Jun. 16, 2005

(65) Prior Publication Data

US 2007/0266778 A1 Nov. 22, 2007

Related U.S. Application Data

(60) Provisional application No. 60/525,312, filed on Nov. 26, 2003.

(51) Int. Cl.
*G01N 15/06* (2006.01)
*G01N 29/00* (2006.01)
(52) U.S. Cl. .................. 73/61.75; 73/1.02; 73/597; 73/645; 422/68.1
(58) Field of Classification Search ............. 73/1.02, 73/1.03, 32 A, 61.75, 597, 627, 645–648; 422/68.1, 102; 702/54
See application file for complete search history.

(56) References Cited

U.S. PATENT DOCUMENTS

| | | | | |
|---|---|---|---|---|
| 4,854,170 A | * | 8/1989 | Brimhall et al. | 73/570 |
| 5,139,328 A | * | 8/1992 | Baker et al. | 356/39 |
| 5,821,399 A | * | 10/1998 | Zelin | 73/1.02 |
| 6,554,788 B1 | * | 4/2003 | Hunley et al. | 604/4.01 |
| 7,018,353 B2 | * | 3/2006 | Hunley et al. | 604/4.01 |
| 2003/0195452 A1 | * | 10/2003 | Hunley et al. | 604/4.01 |

* cited by examiner

*Primary Examiner*—Hezron Williams
*Assistant Examiner*—Samir M Shah
(74) *Attorney, Agent, or Firm*—Ober/Kaler; Royal W. Craig

(57) ABSTRACT

An ultrasonic field-portable system for accurately measuring hematocrit (HCT) and hemoglobin concentration (HGB) in small food samples. The system includes an analyzer (10) that allows extremely accurate measurements of blood hematocrit from only one or two drops of +>>d collected in a disposable sampling device (12) that is then inserted into the analyzer (10). The system is compact enough to package into a point of care device, making it a point of care device with accuracy comparable to larger CBC lab equipment.

20 Claims, 13 Drawing Sheets

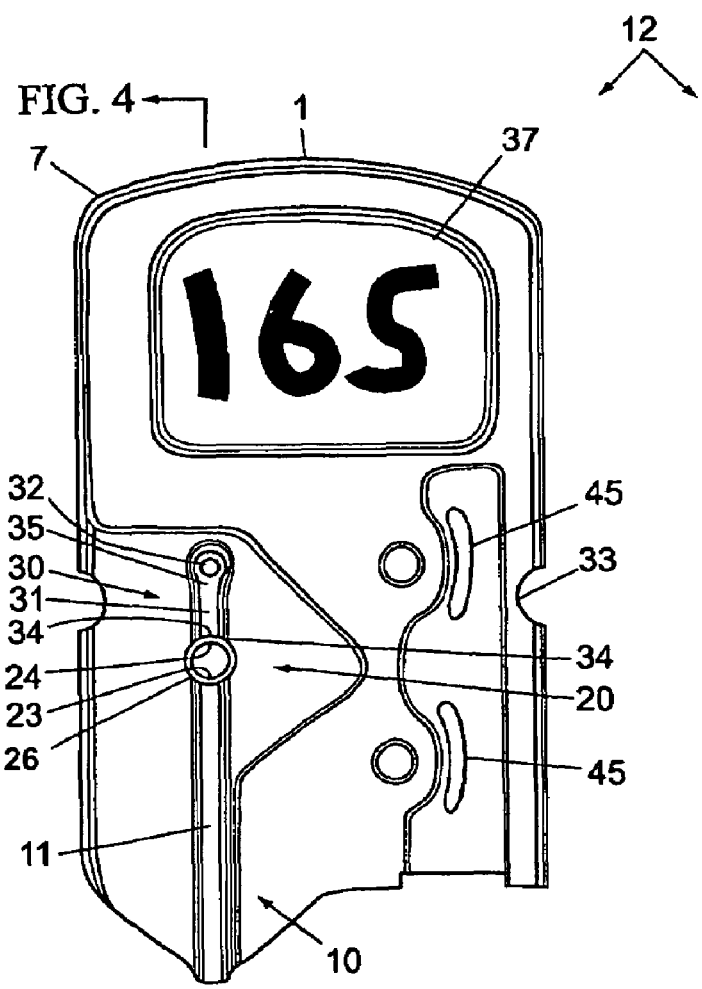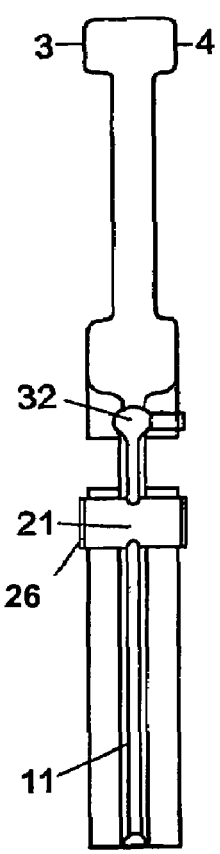
FIG. 6
FIG. 7

METHOD AND APPARATUS FOR ULTRASONIC DETERMINATION OF HEMATOCRIT AND HEMOGLOBIN CONCENTRATIONS

CROSS-REFERENCE TO RELATED APPLICATIONS

The present application derives priority from U.S. provisional application Ser. No. 60/525,312 filed Nov. 26, 2003.

STATEMENT OF GOVERNMENT INTEREST

This invention was made with government support under grant number HL63587-03 awarded by the National Heart, Lung, and Blood Institute at the National Institute of Health. The U.S. Government has certain rights in the invention.

BACKGROUND OF THE INVENTION

1. Field of the Invention

The present invention relates to blood sampling and, more particularly, to the ultrasonic measurement of hematocrit and/or hemoglobin concentration of a small blood sample.

2. Discussion of the Background

Physicians routinely test blood parameters as part of the diagnostic process. The complete blood count (CBC) is the most common of these tests. A CBC measures the status of important features of the blood, including the following: mean corpuscular hemoglobin, which is also called MCH; mean corpuscular hemoglobin concentration, which is also called MCHC; mean corpuscular volume, also called MCV; number of platelets; number of red blood cells (RBCs); number of white blood cells (WBCs); percentage of blood volume composed of red cells, called hematocrit (HCT); and total concentration of hemoglobin in the blood, also called HGB. Physicians use the results to assess the quantity and the condition of the blood's cellular components. For example, the CBC hemoglobin concentration (or HGB, typically stated in g/dl) describes the oxygen-carrying capacity of the red blood cells because HGB is the protein that the body uses to transport oxygen. The hematocrit or "HCT" (measured in a % concentration) is defined as the portion of the total volume of blood occupied by red blood cells. This volume fraction may be expressed as a decimal (e.g., liter/liter) or as a percentage (e.g., liter/liter×100%). HCT measurements typically provide the same information to the physician as the hemoglobin concentration (HGB)—the oxygen carrying capacity of the blood—because under normal physiological conditions almost all of the blood's hemoglobin is in the red blood cells. The Mean Corpuscular Volume (MCV) is the average of the red blood cell volume. The Red Blood Cell Count (RBC) is an expression of the number of red blood cells per unit volume of blood, typically, cells per microliter ($\Box$l). Mean Cellular Hemoglobin (CH) is the average mass of hemoglobin that can be found in each red blood cell. In contrast, Mean Cellular Hemoglobin Concentration (MCHC) is the average concentration (instead of mass) of hemoglobin in red blood cells. The concentration of hemoglobin in a blood cell is simply the mass of hemoglobin divided by the volume it occupies: MCHC=MCH/MCV, meaning that MCHC can be calculated from the MCH and MCV instead of being independently measured. Among the other components of blood that are characterized in a complete blood count include white blood cells and platelets. Whole blood is defined as blood that includes red blood cells, white blood cells, platelets, and all the normal components of blood.

These blood properties, in particular HCT and/or HGB, can be used to diagnose anemia, acute blood loss, dehydration, and scores of other conditions. Physicians routinely monitor HCT both acutely and chronically and may act on changes of as little as two percent (2%) of the measured value.

In the hospital environment, the blood lab routinely performs complete blood counts. Blood samples are drawn into vials and delivered to the central blood lab where an automated system performs the testing. The results are relatively accurate, but not immediately available (typically requires 10 minutes to 1 hour). Alternatively, there are a few handheld blood parameter devices that provide measurements of HCT or HGB at the point of care, but the intrusiveness of the measurement and the relative inaccuracy inherent in these devices limits their diagnostic value.

In the emergency medical environment, there is currently no method to measure HCT or HGB in the field to the same accuracy as the automated blood lab systems. The existing handheld devices noted above are difficult to use or are not sufficiently accurate. Patients requiring a hematocrit measurement, such as victims of trauma or disaster, must await transport to a hospital or clinic with a blood lab before this information can be accurately measured. If accurate results were available in the field, it would improve the ability of medical personnel to triage patients and speed the delivery of appropriate medical care when the patient arrived at the hospital.

In the field, it can be difficult to assess the extent to which an injured patient has bled internally. A patient's HCT decreases with blood loss. Consequently, successive HCT measurements provide a valuable indication of the degree of blood loss. In cases where the emergency medical personnel are overwhelmed by the number of injured, a device which quickly and accurately measures the HCT of those in need of medical care would greatly improve the ability of the emergency medical personnel to focus their attention on critical cases. Thus, the public emergency medical industry and the military have a significant need for a device and method capable of measuring HCT quickly, accurately and at point-of-care.

Private practice physicians who need accurate measurements of HCT are currently limited to sending blood samples to a contract blood lab, or performing slow, imprecise manual techniques that are subject to human error such as spun hematocrit or microscopic inspection.

Four methods are currently available to measure HCT:

centrifuge, cell count, optical characteristics, and electrical characteristics.

The centrifuge method is the most basic measurement technique. These centrifuges are not portable. To measure HCT, a blood sample is drawn and spun in a centrifuge (e.g. READACRIT®) for a fixed duration (typically five to thirty minutes, depending on protocol). The spin separates the blood sample into three layers. The top layer is the plasmas made up primarily of water and dissolved solids. The next layer is the thin buffy coat, made up of white blood cells, plasma proteins, and platelets. The bottom layer contains closely packed red blood cells. A technician reads the volume fraction directly using a scale. Spun hematocrit accuracy can be affected by user error in reading the scale, plasma entrapped in the red blood cell column, and distortion of red blood cell size. Typically, the resulting accuracy of a spun hematocrit performed to protocol is 2 to 5% of the measured value. This accuracy, as with all other accuracies in this report, is reported as the 95% confidence interval around the mean.

Cell counting is the most direct of the measurement techniques. The blood sample is diluted to a known ratio and individual cells are counted either manually or automatically. Manual cell counting techniques are tedious and proper preparation of the sample depends on the skill of the operator. Automated cell counters (e.g. COULTER@ GEN STM System) typically offer 1-minute sample turnaround, claim accuracies to 2.0-3.5% of the measured value, and reduce tedium and operator dependence. As a practical matter, the turnaround time at the point of care is typically 30 minutes to 12 hours, because blood samples must be transported from the patient to the centrally located lab, processed, and the results must be reported back to the point of care. Furthermore, automated systems are typically expensive and are not portable.

The optical measurement technique is relatively new. Devices employing this technique measure the amount of light transmitted through, or reflected from, flowing blood. These devices (e.g. 3M® CDITM System 500) are designed for use during cardiac surgery, require a blood circuit, and are not portable.

HemoCue®, is an example of a handheld device that photometrically measures the blood hemoglobin concentration. Such portable photometric devices have a 1-minute cycle time, but the accuracy is typically around 3%. A portable device with greater accuracy would be valuable because physicians make decisions based on changes as small as 1-2% of the reading.

Electrical conductivity is currently used to measure a variety of blood parameters, including hematocrit. The i-STAT® system, for example, measures the conductivity of a blood sample, corrects for ion concentrations, assumes normal white blood cell and protein levels and then calculates and reports hematocrit. While instruments that use electrical conductivity are portable, the accuracy of a typical conductivity-based hematocrit reading is 6%, which substantially reduces the clinical value.

In the field of blood ultrasonics, much investigation has focused on analyzing ultrasonic backscatter in devices that measure blood flow velocity using the Doppler effect. In contrast, there is much less research on the relationship between speed of sound and hematocrit.

For example, the following references are hereby incorporated by reference:

Edwin L. Carstensen, Kam Li, and Herman P. Schwan, "Determination of the Acoustic Properties of Blood and its Components," The Journal of the Acoustical Society of America Volume 23, Number 2, Pages 286-289 (1953).

Edwin L. Carstensen and Herman P. Schwan, "Absorption of Sound Arising from the Presence of Intact Cells in Blood," The Journal of the Acoustical Society of America Volume 31, Number 2, Pages 185-189 (1959).

Rubens A. Sigelmann and John M. Reid, "Analysis and Measurement of Ultrasound Backscattering from an Ensemble of Scatterers Excited by Sine-Wave Bursts," The Journal of the Acoustical Society of America Volume 53, Number 5, Pages 1351-1355 (1973).

KoPing K. Shung, Rubens A. Sigelmann, and John M. Reid, "Scattering of Ultrasound by Blood," IEEE Transactions on Biomedical Engineering Volume BME-23, No. 6, Pages 460-467 (1976).

Stephen E. Borders, Arnost Fronek, W. Scott Kemper and Dean Franklin, "Ultrasonic Energy Backscattered from Blood," Annals of Biomedical Engineering, Volume 6, pages 83-92 (1978).

S. Xu and H. Ermert, "Models for Describing the Scattering of Ultrasound in Blood," Biomed. Technik, Volume 42 (5), Pages 123-131 (1997).

S. A. Gross, R. L. Johnston, and F. Dunn, "Comprehensive Compilation of Empirical Ultrasonic Properties of Mammalian Tissues" J. Acoust. Soc. Amer., Vol. 64, Pages 423-457, 1987.

Larry Y. L. Mo and Richard S. C. Cobbold, "A Stochastic Model of the Backscattered Doppler Ultrasound from Blood," IEEE Transactions on Biomedical Engineering, Volume BME-33, No. 1, Pages 20-27 (1986).

I. Y. Kuo and K. K. Shung, "High Frequency Ultrasonic Backscatter from Erythrocyte Suspension," IEEE Transactions on Biomedical Engineering, Volume 41, No. 1, Pages 29-33 (1994).

Daniel Schneditz, Thomas Kenner, Helmut Heimel, and Hans Stabinger, "A sound-speed sensor for the measurement of total protein concentration in disposable, blood-perfused tubes," J. Acoust. Soc. Am., Vol. 86, No. 6, Pages 2073-2080 (1989).

K. Kirk Shung, Guy Cloutier, and Chee C. Lim, "The Effects of Hematocrit, Shear Rate, and Turbulence on Ultrasonic Doppler," IEEE Transactions on Biomedical Engineering, Volume 39, No. 5, Pages 462-489 (1992).

These studies are useful for understanding the interaction between ultrasound and blood. Also, many researchers have explored the ultrasonic characteristics of blood for the purpose of better understanding how these characteristics enable or interfere with imaging and sonography devices. However, they suggest no practical implementation for the ultrasonic measurement of hematocrit (HCT) or hemoglobin (HGB) concentrations of a small blood sample using a field-portable device.

Schneditz et al (U.S. Pat. No. 5,830,365) built a sound-speed sensor and evaluated it as a method for measuring total protein concentration in a tube of flowing blood. The device is intended to track fluid shifts in a patients blood as they are on a hemodialysis machine. These fluid shifts would manifest themselves as a change in total protein concentration. Schneditz investigated the correlation between total protein concentration and speed of sound in order to detect these fluid shifts. He implemented a speed of sound measurement by measuring time of flight along a single direct path. A disadvantage of the Schneditz device is that it only works with continuously circulating blood from the patient and back into the patient (such as, for example, in an inline hemodialysis apparatuses), where the blood is continuously flowing in order to avoid settling of the blood cells from; the plasma, which would cause inaccurate readings. Another disadvantage is that it requires a large volume (60 mL) of blood circulating through tubing from a thermostatted 500 mL bath, and it requires calibration with reference fluids whose speed of sound was known accurately. Again, these considerations limit the effectiveness for rapid deployment in the field. Moreover, the Schneditz device has been implemented on porcine blood (pig blood) with the white blood cells artificially removed (along with any other blood components in the white blood cell layer). The absence of white blood cells and the physical differences between porcine blood and human blood may significantly alter the ultrasonic response of the blood and therefore the Schneditz et al correlations and methods may not apply to whole or human blood. What is needed is an approach that can be implemented in a hand-held device, using only 1 drop of blood, and yet still provide high-accuracy measurement of hematocrit and/or hemoglobin concentration. None of Schneditz nor any of the foregoing or other known apparatus or methods solve the combined problems of speed, accuracy, and portability in hematocrit or hemoglobin concentration measurement. Moreover, in order to sonically measure HCT concentration with accuracy, it is also necessary to either measure or control the temperature of the blood sample. Conventional methods for controlling temperature, including thermostat-controlled baths are cumbersome and impractical. Other methods for measuring, such as directly contacting the blood with a temperature probe, lead to cleaning and contamination complications. As such, there also remains a need for effecting an accurate and efficient temperature measurement of a small blood sample in a field-portable device.

The present invention accomplishes all four goals, namely, speed, portability, proficient temperature measurement, and high-accuracy measurement of hematocrit and/or hemoglobin concentration, simultaneously in a field-capable device.

SUMMARY OF THE INVENTION

Accordingly, one object of the present invention is to provide a system inclusive of method and device for measuring the hematocrit (HCT) or hemoglobin concentration (HGB) of blood.

It is another object of the present invention to provide a system as described above that will allow simple, accurate, and quick measurements of HCT and HGB concentration.

It is another object of the invention to provide methods and apparatus that can measure the HCT and HGB to within +/2% (of reading) accuracy with a 95% confidence interval.

It is another object of the present invention to provide a system as described above that can provide a measurement within 30 seconds.

It is another object of the present invention to provide a system that utilizes a blood draw of less than 1 ml, and is preferably optimized for using a drop of capillary blood (although venous blood is also suitable).

It is another object of the present invention to provide a device that is battery-operated, portable and small enough to be hand-held.

It is another object of the present invention to provide a device that is small enough to be incorporated into an automated, non-handheld, multi-function analyzer.

In accordance with the foregoing objects, the present application describes a system inclusive of method and apparatus for measuring the HCT and HGB of blood using ultrasonics. The method generally includes the steps of taking a discrete whole blood sample using a collection device, introducing the collection device (with sample) into a portable analyzer, activating the analyzer to generate one or more ultrasonic signals (e.g, pulses) into the blood sample (while still contained in the collection device), and detecting transmissions/reflections therefrom. The temperature of the sample is also measured by the analyzer. The ultrasonic characteristics, such as speed of sound (SOS), backscatter, or attenuation are determined from the transmissions/reflections, and the clinical parameter HCT and/or HGB is calculated from the combined ultrasonic and temperature parameters.

In operation, the general method is implemented as follows by the present apparatus which includes a physical field-portable analyzer for accepting and accurately measuring hematocrit (HCT) and/or hemoglobin (HGB) in small blood samples, inclusive of electronics, software and internal configuration for generating ultrasonic pulses into the blood sample, measuring speed of sound there from as well as temperature of the blood sample, calculating HCT and/or HGB from the speed of sound and temperature measurements, and displaying the HCT or HGB measurement to a user. The present apparatus also includes a sample collection device for collecting a small discrete blood sample. The analyzer has a sample chamber to which the sample collection device docks to expose the blood sample to a transducer. The transducer emits an ultrasonic pulse to the blood in the sample chamber, and receives one or more reflected ultrasonic signals from the blood sample. The transducer is connected to a circuit board which contains signal conditioning and processing circuitry for measuring speed of sound from the reflected ultrasonic signals, and for calculating based on said measured speed of sound HCT and/or HGB.

The system is fast and accurate to as little as 1% as verified by international reference standards. In addition, the invention is suitable for minimally-invasive measurements (using the blood sampling device to place a very small blood sample in the measurement chamber). The blood sampling device can be a disposable unit to safely and conveniently introduce a small blood sample into the analyzer. The system attributes as described above are reflective of the very first point of care HCT and/or HGB measurement device with accuracy comparable to larger CBC lab equipment.

BRIEF DESCRIPTION OF THE DRAWINGS

Other objects, features, and advantages of the present invention will become more apparent from the following detailed description of the preferred embodiments and certain modifications thereof when taken together with the accompanying drawings in which:

FIGS. 6-9 illustrate a front view, section view, end view, and side perspective view, respectively, of an exemplary disposable sampling device 12 used in conjunction with the field-portable analyzer 10 of FIGS. 1-4.

DESCRIPTION OF THE PREFERRED EMBODIMENTS

Figure 1:
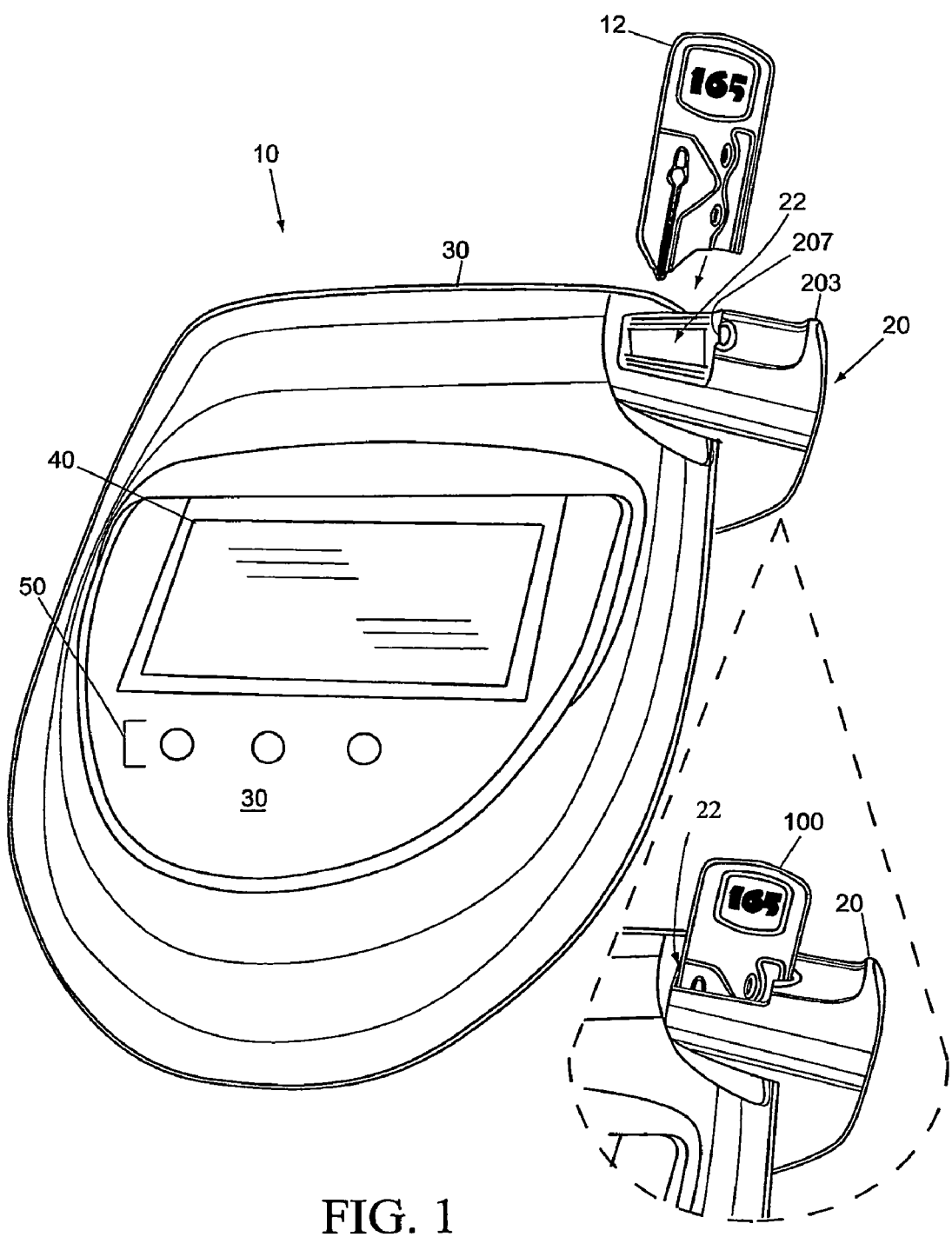
FIGS. 1-4 are a front perspective view, right side view, bottom view, and back view, respectively, of the field-portable analyzer 10 according to the present invention.

The present invention is a system inclusive of method and apparatus for measuring the HCT and HGB concentration of blood using ultrasonics. The preferred embodiment described herein is the very first point of care HCT and/or HGB measurement device with accuracy comparable to larger CBC lab equipment.

FIGS. 1-4 are a front perspective view, right side view, bottom view, and back view, respectively, of the system inclusive of field-portable analyzer 10 and disposable blood sampling device 12 in accordance with the present invention. With combined reference to FIGS. 1-4, the present analyzer 10 accepts the disposable blood sampling device 12 (containing a small blood sample) in a sample door 20. Door 20 is closed, and an automatic test sequence is carried out by which the analyzer 10 accurately measures the hematocrit (HCT) and/or hemoglobin (HGB) from the blood sample, which remains safely contained within the disposable 12. Analyzer 10 is a point of care HCT and/or HGB measurement device of hand-held size, and generally includes a portable housing 30 having a battery pack (obscured) seated in a downwardly protruding rear stand 32. The sample door 20 is side-oriented door pivoted to the housing and formed with a contoured sample chamber 22 for convenient guided-insertion of disposable 12. The sample door 20 latches shut to precisely align and lock the disposable 20 in place in a sample chamber (to be described). A set of sealed pressure-sensitive control keys 50 allows user-control of the testing process. In the illustrated embodiment three keys 50 are provided, one for device ON/OFF, one for test initiation, and one for calibration and diagnostics. All three keys 50 are coupled to an internal circuit board (as will be described) that seats a processor and memory (thus keys 50 may be alternately programmed as desired). A, LCD display screen 40 displays the device status and the measured HCT and/or HGB concentration of the blood sample to the user. The housing 30 encloses the battery pack as well as the circuit board on which a processor and a plurality of supporting electronic components reside for initiating the test sequence. The test sequence includes generating ultrasonic pulses into the blood sample (still in disposable sampling device 12), measuring time of flight of said ultrasonic pulses through the blood sample, as well as temperature of the blood sample, calculating HCT and/or HGB from the speed of sound and temperature measurements, and displaying the HCT or HGB measurement on the display screen 40.

The disposable sample collection device 12 (described in detail below) is used for collecting a small discrete blood sample and for containing it while it is introduced safely and effectively into the analyzer 10 via door 20. The door 20 is spring-biased open, and latches shut to place the disposable 12 inside a sample chamber 22. Once inside the sample chamber 22 the blood sample in disposable device 12 is pumped into a test cell (within the disposable 12) where it exposed to a transducer in the analyzer 10 for making the ultrasonic speed of sound measurements of the present invention. The internal circuit board contains signal conditioning and processing circuitry for measuring the speed of sound from the reflected ultrasonic signals, and for calculating (based on said measured speed of sound) the HCT and/or HGB concentration. At the culmination of the testing, the door 20 is automatically unlatched and swings open for removal of the disposable 12.

Figure 2:
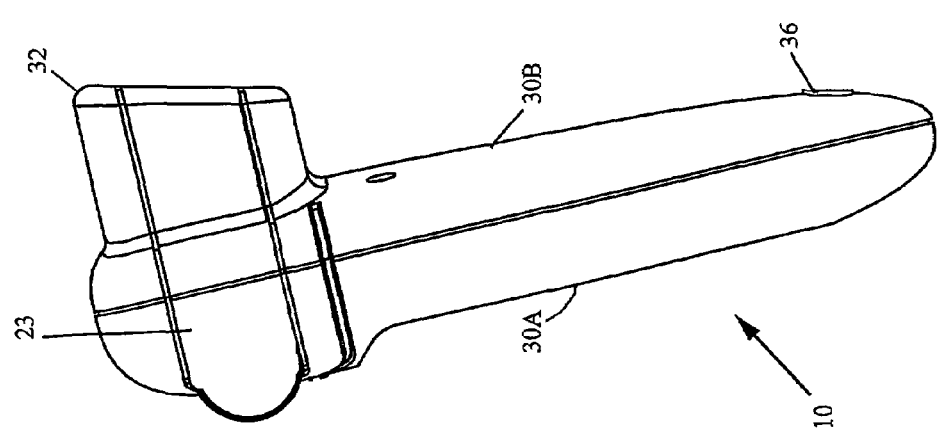

As best seen in FIG. 2, the portable housing 30 may be formed from two molded and interfitting clamshell sections 30A & 30B, the back section 30B having a downward protrusion 32 that doubles as a rear stand and as an enclosure for a battery pack (or conventional battery cells). Preferably, a pair of rubberized foot pads 36 are placed opposite the protrusion 32 of the back section 30B to create a secure footing on flat surfaces.

Figure 3:
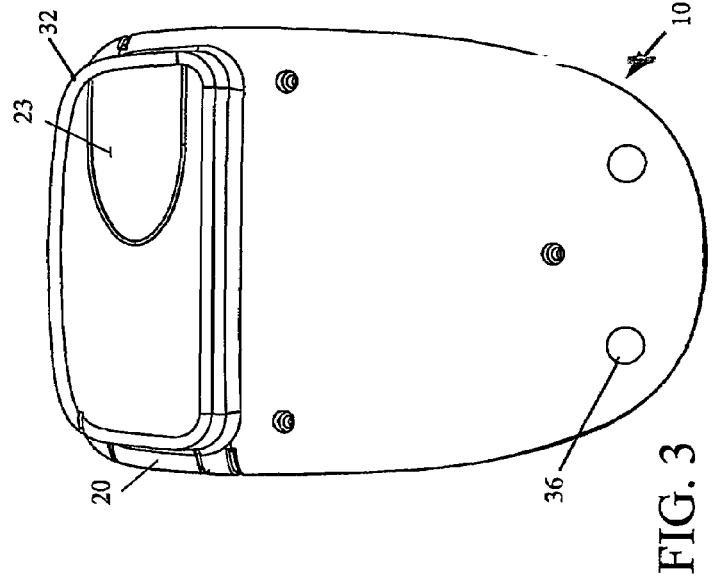

As seen in FIG. 3, one side of both clamshell sections 30A & 30B at protrusion 32 are defined by an alcove in which the door 20 is pivotally mounted, such that when the door 20 is latched shut it conforms to the outward aesthetic of the housing 30. The door 20 may be removed from its hinges to clean the sample chamber and/or sensors. A removable panel 23 provides access through the downward protrusion 32 of back section 30B for rear access to the enclosed battery pack.

Figure 4:
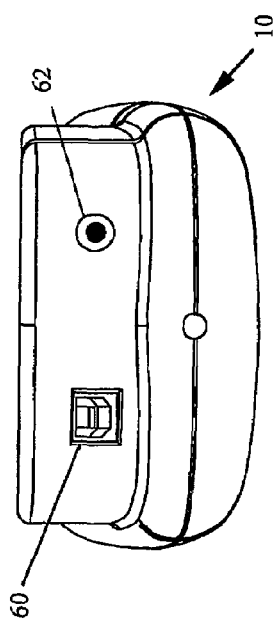

As shown in FIG. 4, a communication port 60, for example, a universal serial bus or other standard computer communication port is panel-mounted at the rear of housing 30 to allow a user to connect a remote computer to the internal circuit board for remote diagnostics, data downloading, and other purposes. A power port 62 is also panel-mounted on the rear of the housing for connecting the device to power outlet via a plug-in transformer.

Figure 5:
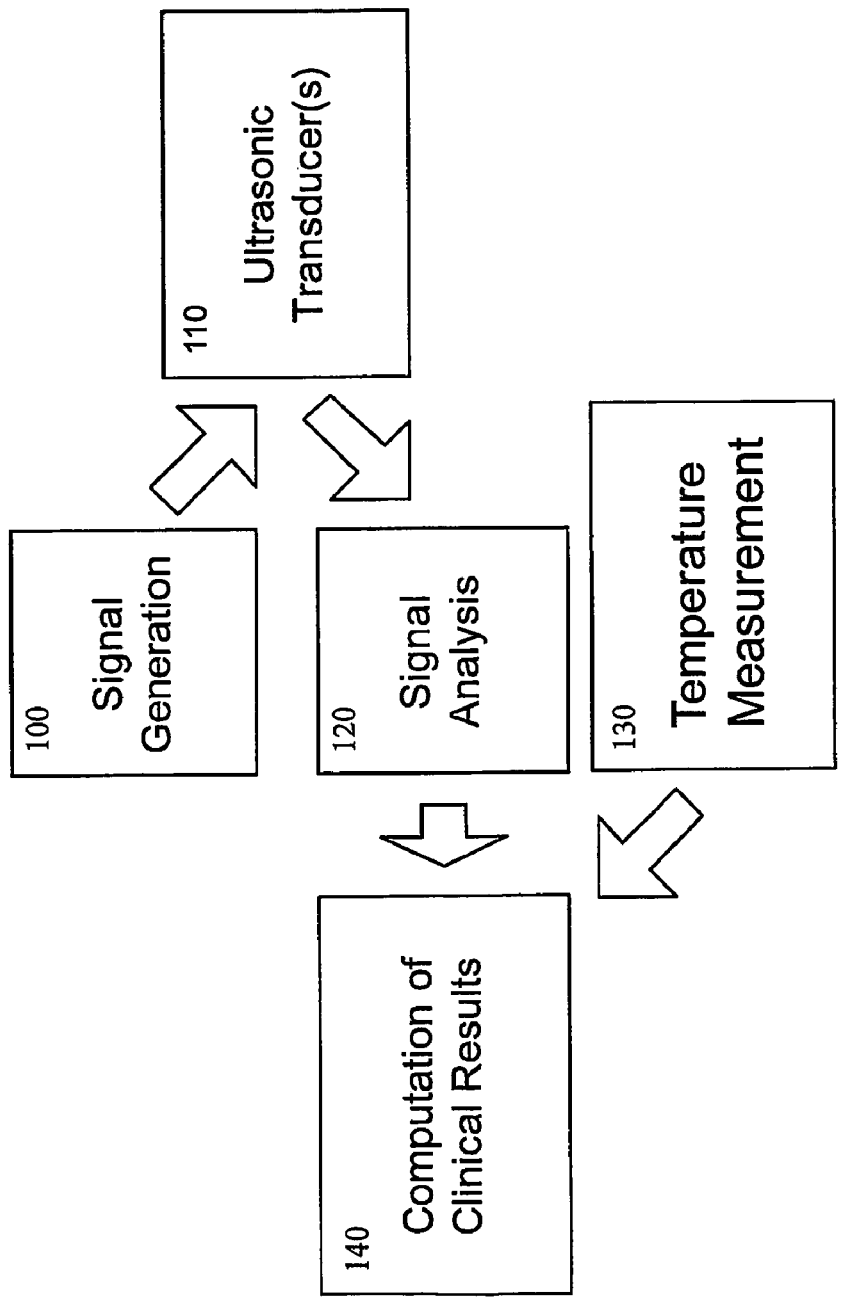
FIG. 5 is a block diagram outlining the HCT and/or HGB concentration measurement method employed by the field-portable analyzer 10 of FIGS. 1-4.
Figure 8:
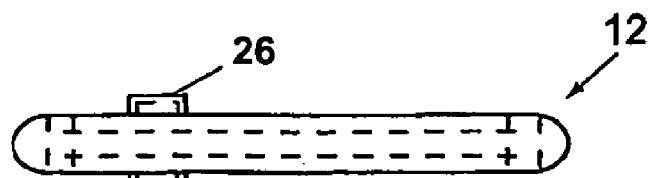

FIG. 5 is a block diagram outlining the HCT and/or HGB concentration measurement method of the present invention. The method is preferably based on a speed of sound technique: measuring the time of flight of ultrasonic signals transmitted into the blood sample and reflected back. The method includes the steps of generating one or more electrical signals at step 100. At step 110, one or more transducers are used to convert the electrical signals to ultrasonic signals (pulses), to subject the whole blood sample to the ultrasound, and to detect transmissions/reflections there from. At step 120 the time of flight through the blood sample is determined from the time differential between the transmissions/reflections. At step 130, the temperature during testing of the blood-sample is determined. At step 140 the speed of sound characteristics are used in combination with a temperature compensation to determine the related clinical parameters: HCT and HGB. The calculation employs a correlation between the clinical parameters and the physical measurements The ultrasonic hematocrit measurement method and apparatus of the present invention can provide measurements of hematocrit and hemoglobin concentration to at least 7% and as little as 1% as verified by the existing international reference standard, substantially in real time. Thus, as compared to other devices that measure the blood properties, the present invention can be implemented in a portable package and achieves clinically significant improvements of accuracy over other portable devices and automated cell counters. Furthermore, the invention provides immediate results at the point of care.

The internal system architecture for implementing the foregoing technique preferably includes an electronics subsystem enclosed within the analyzer 10, associated software, and the disposable sampling device 12 (as will be seen, the disposable 12 becomes part of the test configuration), and a door latching mechanism for seating the disposable 12 in a sample chamber in analyzer 10 for testing. Disposable 12 is inserted into door 20, which is then closed to introduce the disposable 12 into a sample chamber (to be described) for carrying out the tests. The electronics subsystem includes conventional microprocessor with supporting chipset and memory for controlling all aspects of the test procedure, plus a micropump for interfacing with the disposable 12 to move the blood sample into position. The electronics subsystem also includes the testing components inclusive of transducer for generating ultrasonic pulses into the blood sample (while contained within the sampling device 12) and for sensing the speed of sound (time of flight of the ultrasound pulses), plus a temperature probe 90 for sensing the temperature of the blood sample. The processor calculates HCT and/or HGB from the speed of sound and temperature measurements, and displays the HCT or HGB measurement to a user via display 40. These features are described in greater detail as follows:

Sample Collection Device 12

In accordance with the present invention; the sample chamber in which the blood is tested and the sampling device in which it is collected are one and the same, the sample collection device 12 acting as the sample chamber upon which the ultrasound method is used. Preferably, the sample collection device 12 is disposable to minimize the amount of cleaning necessary. On the other hand, it is also preferable that the blood in sample collection device 12 directly contacts the surfaces of the sample chamber in analyzer 10 in order to create the acoustic coupling necessary to transmit and receive sound from the blood. Direct contact is important because it allows the device to control and compensate for the exact distance through which the ultrasound travels through blood. Knowledge of that distance facilitates an accurate calculation of speed of sound from a time of flight measurement. The preferred embodiment described below accomplishes both, fully containing the blood within disposable 12 during testing, and yet allowing direct contact of the blood with the surfaces of analyzer 10.

FIGS. 6-9 illustrate a front view, section view, end view, and side perspective view, respectively, of an exemplary sampling device 12 used in conjunction with the field-portable analyzer 10 of FIGS. 1-4. The sampling device 12 is a disposable unit for safely and conveniently introducing a small blood sample into the analyzer 10.

The sampling device 12 generally comprises an elongate and relatively thin rubber supporting frame 7 including a finger grip end and opposing functional end formed with various functional features segregated into three primary regions, a collecting region 10, a testing region 20, and an actuator region 30. The entirety of sampling device 12 may be molded of Pebax rubber by Atofina Co., or any other flexible elastomer.

The collecting region 10 comprises an entrance aperture to a capillary tube 11 that, in the preferred embodiment, is a hollow hydrophilic cylindrical tube with a volume of approximately 50 micro-liters (this is suited for collecting approximately 1-2 drops of blood). However, depending on the particular analyzer for which the device is designed, the volume of the capillary tube 11 may vary from between 0.01-1 ml. The presently preferred dimensions for the capillary tube 11 are cylindrical with an inner diameter of 1.6 mm and a length of 19 mm, although other dimensions and shapes may be suitable. The length and inner diameter can be increased to collect a larger sample, or they can be decreased in order to wick more quickly and ensure that the receptacle holds the sample securely. The capillary tube 11 may have a circular cross-section as shown, or oval or various rectilinear shapes. It has been found that a non-circular cross-section such as a star or rectangle augments the capillary draw of the tube 11, but may be more difficult to mold. The entrance aperture of capillary tube 11 protrudes outward for easier collection. Capillary tube 11 continues into a testing region 20 (see below). The walls of the capillary tube 11 are relatively clear or translucent and may be demarcated by visible indicator lines, graduated markings or some other obvious feature to indicate to the user that enough blood has been acquired. In practice, a patient's blood will be drawn by a pin prick (as described below), the entrance aperture of capillary tube 11 will be placed in contact with the blood, and the blood will be inducted by capillary action into the tube 11 until a sufficient quantity is collected. Once done, the capillary tube 11 serves as the temporary storage receptacle for the blood during transit from the patient to the analyzer 10.

Figure 9:
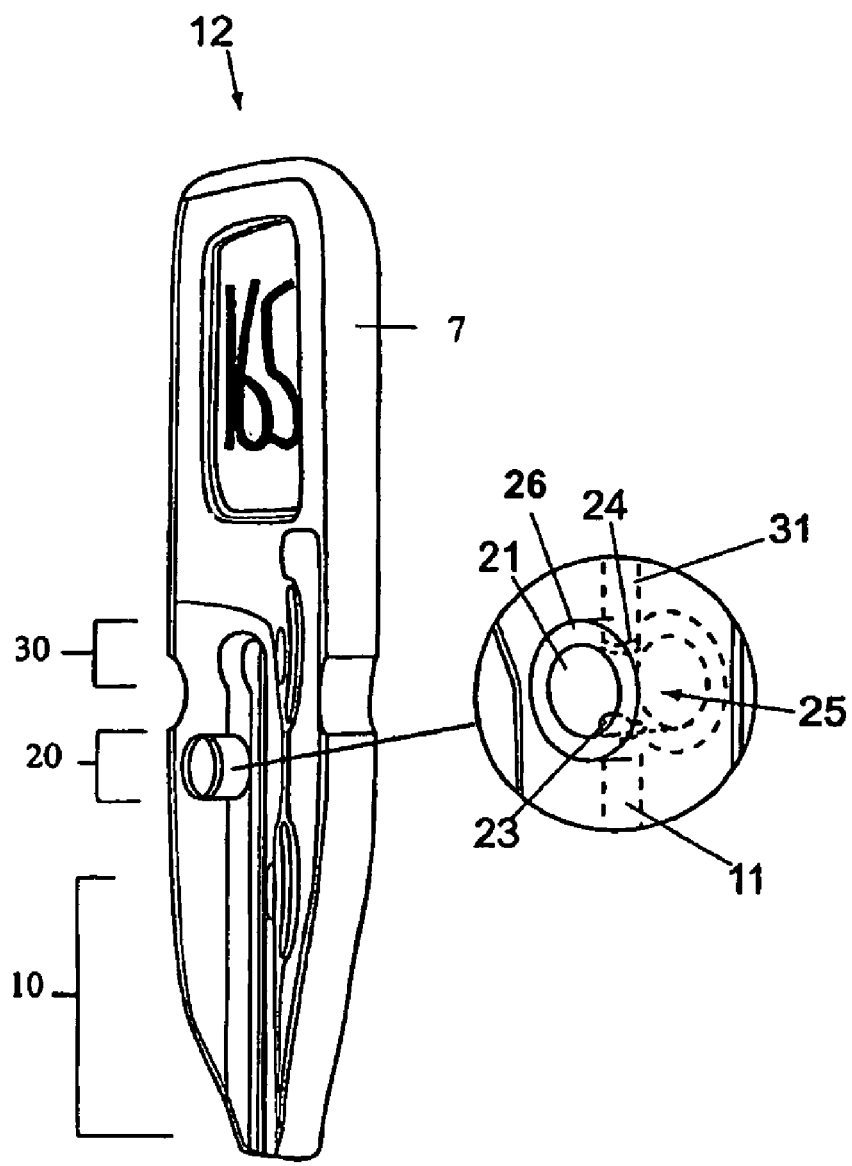

The enlarged illustration to the right of FIG. 9 illustrates the connection between the opposing end of tube 11 and testing region 20 of the disposable device 12. The testing region 20 is an open window formed by a transverse aperture 21 through the front and back of the supporting frame of the sampling device 12. Preferably, the aperture 21 is cylindrical to define a round-walled testing channel 25 with cylindrical cross-section. Square or rectangular cross sections are also suitable, but a cylindrical shape (round aperture with flat sides) deters air bubbles from forming in the testing channel 25, while also minimizing the amount of blood required for accurate testing. Two rims surround the aperture 21 on both the front and back surface and these are slightly raised to form sealing rings 26 (see FIG. 8) against the walls of the analyzer 10. The sealing rings 26 form the contact points with the sampling device 12 when it is inserted into the analyzer 10 and the door 20 is latched shut to lock the sampling device 12 in place. Disposable device 12 is squeezed tightly between two walls of the sampling chamber inside the analyzer 10, said walls mating with the sealing rings 26 to hermetically seal off the testing channel 25. The volume of the sealed testing channel 25 may range from 0.01 to 1 ml.

The passage of the capillary tube 11 traverses the testing channel 25 at two holes 23, 24 located opposite each other. The far hole 24 continues into the actuator region 30 via a hollow actuator tube 31. As shown in FIG. 6, the actuator tube 31 leads to an actuator orifice 32 that is open through the front of the sampling device 12. Orifice 32 seals over a connection to a small micro-pump (described below) in analyzer 10 that, when activated, draws the blood sample from capillary tube 11 into the sealed testing channel 25.

The capillary tube 11 is vertically-oriented, a substantially vertical orientation of the device 12 is maintained while in the analyzer 10 so that any entrapped air bubbles will migrate up the capillary tube 11 through the testing channel 25 and out the orifice 32.

The actuator tube 31, including ends 34 and 35, is integrally molded (or attached and sealed) at end 34 to the edges of hole 24 of testing channel 25, and this may be accomplished by molding and welding two half-sections or by unitary molding of the entire device 12. In a similar manner to the raised rims around the testing aperture 21, a raised rim exists around the actuating orifice 32. As the sampling device 12 is inserted into the analyzer 10, this rim forms a seal around a mating hole on the wall of the analyzer (not shown), allowing the micro-pump to communicate with the sampling device 12 and pull the fluid up from the collecting region into the testing region.

The disposable 12 is molded with a pair of crescent-shaped apertures 45 on one side. Crescent-shaped apertures 45 add resiliency and allow a degree of compression between the analyzer 10 housing 30 and door 20, helping to create a positive latching effect and securely seating the device 12 in the analyzer 10.

The grip end 1 of the disposable 12 may include one or more raised or textured finger grips or raised text 37 (i.e.

ridges or bumps) to help prevent dropping of the device during blood collection and transfer to the analyzer 10.

While the preferred embodiment of the disposable device 12 is made generally of hard rubber with integral rubber sealing rings 26, one skilled in the art will understand that the device 12 may be formed substantially of hard plastic with separate rubber grommet-type sealing rings 26. Other possible materials include glass, polystyrene, polyamide, polyvinylchloride, polycarbonate, silicone, polypropylene, polyurethane, latex or polyethylene. The choice of materials and surface finishes for the device 12 are preferably chosen to prolong the onset of coagulation (i.e. Pebax is suitable). This is particularly desirable when using untreated capillary blood in an ultrasonic analyzer because it has been demonstrated that the biochemical process of coagulation changes the speed of sound over time. Surface finishes are preferably smooth to minimize the surface area, allowing the blood to flow more freely through the device and prolong the onset of coagulation.

The sampling device 12 may be manufactured by one-shot molding, or two-shot molding in separate halves that are then hot-welded together, the sealing rings 26 and other flexible components being integrally molded or added separately. The various parts may be connected by snaps, adhesive, ultrasonic welding, or any other method of securing differing plastic or rubber materials. The sampling device 12 may also be formed using blow molding.

The sampling device 12 will function with a drop of venous blood, but more preferably it is optimized for application with capillary blood. Capillary blood tends to have a slightly different mixture of components than venous or arterial blood. For example, the HCT and HGB of sampled capillary blood is typically 2-5% higher than a sample taken from the vein, a significant difference that may cause a doctor to make a different decision. It is also noteworthy that venous blood is typically treated with anticoagulant such as EDTA which is built directly into the test tube, whereas capillary blood is preferably tested without anticoagulant to simplify the collection process for the user. Accordingly, the interpretation of ultrasonic signals and correlations are preferably tailored to the type of draw. The advantage of capillary blood is that it can be drawn from the patient's finger quickly and safely whereas puncturing a vein is a much more involved procedure, putting the patient at greater discomfort and greater risk of complication. The analyzer 10 is optimized to work with the small volumes of blood available from a finger stick by using techniques as reducing the beam angle and increasing the time resolution of the measurement.

In use, a drop of capillary blood is preferably drawn from a finger by lancing the skin (i.e. by finger, heel or ear lobe stick) to obtain a capillary blood sample in the disposable 12 (as opposed to venous blood which is drawn directly from a large vein in the arm to fill an entire test tube). The end of capillary tube 11 is placed immediately adjacent to the incision site and the blood is drawn into capillary tube 11 by capillary action. When the user sees through the clear or translucent capillary tube 11 that enough blood has entered the tube (e.g., blood has reached an indicator line or the end of the tube), the device is moved away from the incision site. Capillary tube 11 then serves as the temporary storage receptacle, until the device 100 can be inserted into analyzer 10 for analysis. Reducing the time between blood draw and completion of the analysis to less than 2 minutes reduces the influence of coagulation on the speed of sound traveling through blood and, thus, the results of ultrasonic blood analysis. If it is anticipated that the time between drawing blood and test completion will be significant (i.e. longer than 2 minutes, thereby causing coagulation which effects the speed of sound through the blood), powdered heparin anticoagulant, EDTA or other anticoagulants, may be coated inside the device to retard coagulation without distorting red blood cells.

The frame structure of the disposable device 12 is specifically designed to mate with sample chamber 22 of the analyzer 10 (See FIGS. 1 and 2), and the sample chamber 22 requires certain structure to work with the device 12. The sample chamber 22 structure includes the door 20 hinged to the main housing 30 of the analyzer 10 and closing and latching shut to capture and seat the sampling device 12 inside with one or more sensors 227 directed orthogonally through (and sealing off) the test cell 25 of the disposable 12 as shown in FIG. 9. Thus, the disposable device 12 is inserted into sample chamber 22 with blood sample already in the capillary tube 11.

Figure 10:
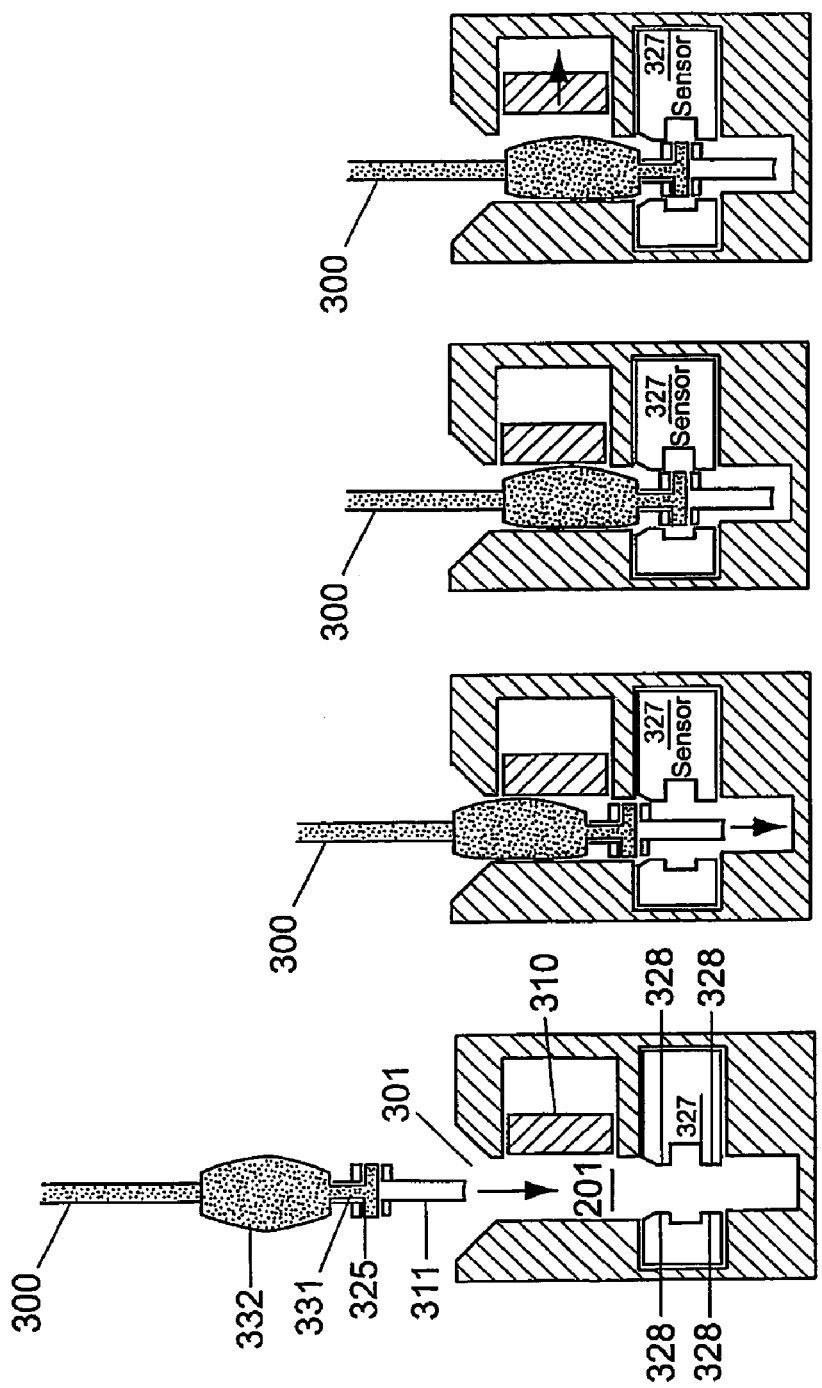
FIG. 10 is a composite drawing of an alternative disposable embodiment 300 in which the micro-pump in analyzer 10 is replaced by an on-board actuator bulb 332 on the disposable 300.

While the embodiment of FIGS. 6-9 relies on a micro-pump engaged to the disposable 12 orifice, FIG. 10 is a composite drawing showing an alternative disposable embodiment 300 in which the action of the micro-pump in analyzer 10 is replaced by an on-board actuator bulb 332 on the disposable 300. The actuator bulb 332 is preferably made of flexible rubber or plastic and may be integrally molded in the sampling device 300 (by molding and welding two half-sections or by unitary molding of the device 300). The actuator bulb 332 is sealed and feeds a pressure differential through a connected actuator tube 331 into testing chamber 325. The actuator bulb 332 protrudes above the plane of the device 300, and the sample chamber 22 is formed with constricted sides (or protrusions) at a predetermined depth. Thus, as device 300 is inserted, the sides of the sample chamber 22 depress the actuator bulb 332 forcing air through actuator tube 331 into testing chamber 325 and out apertures 321, and then releases the bulb 332 as the bulb travels past. This way, when the device 300 is inserted into sample chamber 22 with blood sample already in the capillary tube 11, the walls of the sample chamber 22 squeeze and release the bulb 332. As before, sealing rings 26 around the testing chamber 325 act as a wiping mechanism against the sensor housing surfaces 328 (which contain one or more sensors 327) within the analyzer 300. Rather than constricted walls, the analyzer 10 may comprise a mechanism 310 for depressing and releasing the actuator bulb 332 as shown (this may be a conventional solenoid). Either way, this creates a vacuum which draws the blood stored in the capillary tube 311 into the testing chamber 325. Once the analysis is complete, the sampling device 300 is withdrawn, the sides of the sample chamber 22 are again positioned to depress the actuator bulb 332, thus using air pressure to force the blood out of the testing chamber 325 and back into capillary tube 311. As the device 300 is removed from the analyzer 10, the sealing rings 26 again serve as a wiping mechanism, cleaning off the sensing surfaces 328. The danger of inadvertent exposure to the blood is eliminated by the sequential use of capillary action and pressure-differential to move the blood from containment, to sample chamber, and back, automatically upon insertion and withdrawal.

In all the above-described embodiments the collection region 10, testing region 20 and the actuation region 30, respectively, have been oriented vertically from the bottom to the top of the supporting frame 7 of the device, but this is not an absolute requirement. The orientation of the functional regions of the device (i.e. the collection region 10, the testing region 20 and the actuation region 30) may be changed depending on the structure of particular analyzer with which the device will interface. The foregoing configuration of sampling device 12 as well as other possible variations are more fully disclosed in a co-pending PCT application filed 5 Nov.

2004 and entitled "Disposable Fluid Sample Collection Device". While the preferred embodiments of the sampling device 12 are custom devices that both collect and hold the blood sample (this is the most expedient and sanitary approach), one skilled in the art will understand that the sampling device could alternatively be an off the shelf syringe or lance, any of which are capable of introducing a small blood sample into the sample chamber of the analyzer 10. Further, the sampling device and sample chamber may comprise a tubular arrangement such that the blood is collected from the patient using a venipuncture needle or other needle device, whereupon the blood flows through a length of tubing. The length of tubing can act as the sample chamber, particularly for the attenuation coefficient and speed of sound measurement methods performed on a sample flowing through the length of tubing. In any event, a calibration can be obtained using samples of independently measured hematocrit, permitting the measurement of the HCT, MCV and/or RBC of the sample, even when flowing through the sample chamber.

Sample Chamber 22 and Transducer(s) 227

Figure 12:
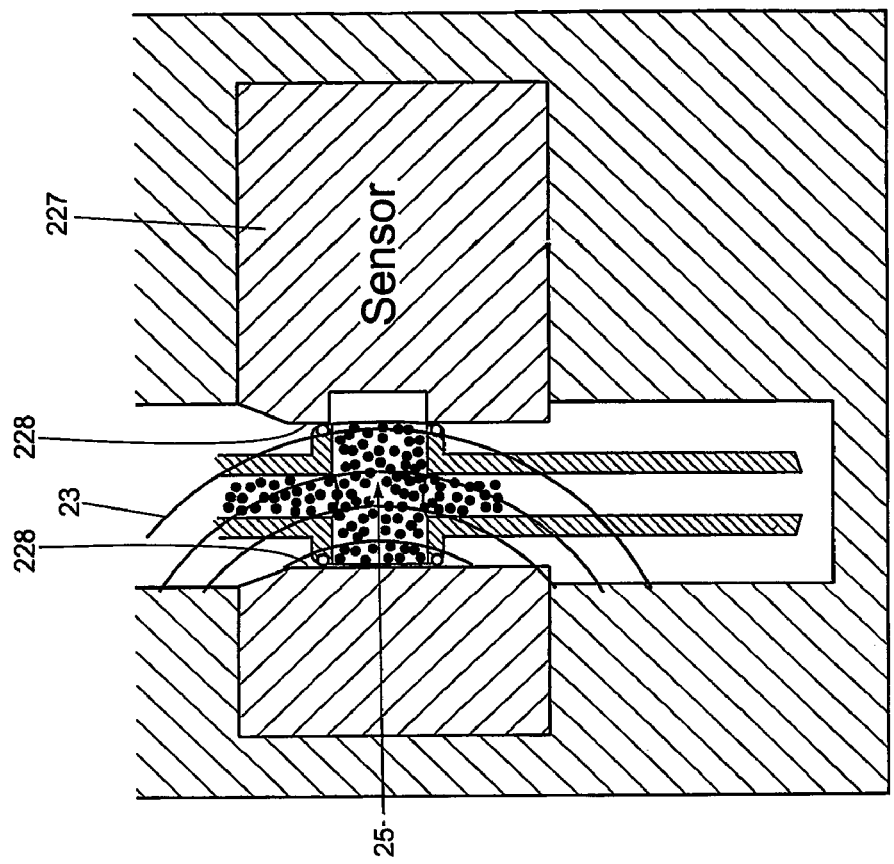
FIG. 12 is an operational schematic of the disposable sampling device 12 in the sampling chamber 22 of analyzer 10.
Figure 11:
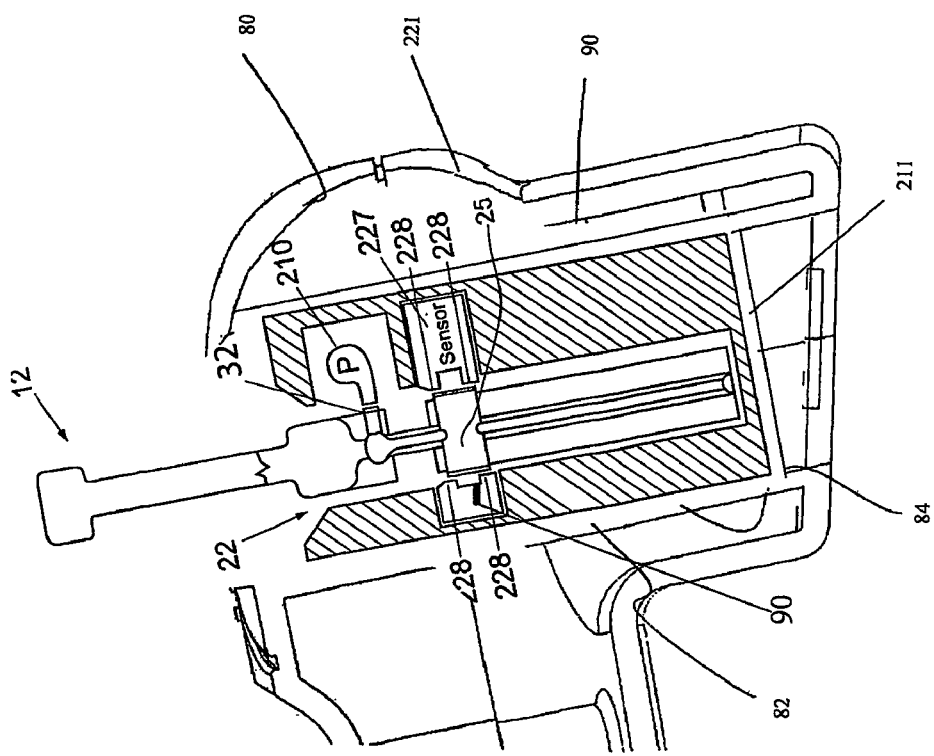
FIG. 11 is a side cross-section illustrating the interface between the disposable sampling device 12 and the sampling chamber 22 of analyzer 10.

FIG. 11 is a side cross-section illustrating the fit of the disposable sampling device 12 in the sample chamber 22 of analyzer 10, and FIG. 12 is an operational schematic. The sample chamber 22 contains one or more transducers 227 having raised sensing surfaces 228 that engage the sealing rings 26 of device 12, the sealing rings 26 acting as a wiping mechanism, cleaning the parallel sensing surfaces 228 of the sensors 227 within the analyzer 10. When fully inserted, the disposable 12 bottoms out in door 20 guaranteeing that the disposable 12 is located correctly with respect to the sensing surfaces 228. The sealing rings 26 then form a hermetic seal against the sensing surfaces 228, thereby forming a closed test cell 25. FIG. 11 illustrates the final position of the disposable 12 with micropump 210 facing the actuator region 30 and raised sensing surfaces 228 around sensor 227 engaged with the sealing rings 26 so that the sensor 227 communicates with the testing channel 25. Micro-pump 210 may be any of a variety of commercially-available micro-pumps such sold by Micropump, Inc., such as their leak-free sealless magnetic drive low flow pumps for metering and dosing liquids.

Again, latching the door 20 activates a microswitch (not shown) that in turn initiates a pumping sequence at micropump 210 to draw the blood in capillary tube 11 into the test cell 25. As seen at FIG. 11, the micro-pump 210 engages actuator orifice 32 and sucks the blood sample out of capillary tube 11 into testing cell 25.

The transducers 227 are included on one side of the sample chamber 22 behind optional window 84 for sending and receiving ultrasonic signals. Additional transducers may be mounted on the opposite face of the gap to facilitate a pitch-catch measurement, although this is not incorporated in the preferred embodiment to eliminate the cost of additional sensors. The transducers 227 are preferably focused or narrow beam angle to avoid significant amounts of energy impacting the edges of the aperture—which could create coherent noise caused by stray paths or diffraction patterns depending on the geometry of the sample chamber. Preferably, transducers having center frequencies of approximately 1 MHz to 50 MHz, more preferably 5 to 20 MHz may be used. 10 MHz transducers are most preferred, however. The higher frequency transducers accommodate a shorter path length, more precise timing, narrower beam angle, and reduced sensitivity to coherent noise.

Transducer 227 element diameter is another factor in determining the beam width. For all configurations and measurements, the transducer element 227 diameter is preferably selected to ensure that the beam angles are appropriate for the shape of the chamber. The beam angles should be narrow enough to minimize the chance of undesired sound paths or diffraction patterns interfering with the measurement (due to sound energy impacting the edges of the aperture).

Furthermore, the transducer 227 element diameter affects the shape of the sound field such as the near field distance. Generally, it is preferred that the echoes are well past the near field by the time they return to the transducer 227 so that the shape of the sound field is simple (it can be approximated by a plane wave). It is even more preferred that the sound is in the far field before it even reaches the blood sample. The window 84 preferably serves the dual purpose of delaying the wave until it reaches the far field in addition to protecting the face of the transducer 227. Because the diameter of the transducer 227 affects the length of the near field, it is preferably chosen in combination with the length of the window 84 to guarantee that the near field is shorter than the transit distance to the blood sample. Smaller diameter transducers will have a shorter near field as in known to those practiced in the art of ultrasonics. Preferable materials for the delay line include plastics or other materials that can create an impedance match to water, have high durability, and low attenuation. Array, focused or narrow-beam-width transducers may help reduce beam width and far-field distance. Some preferred transducer diameters include 1.5 mm, 3 mm, 6 mm, and 12 mm. The transducer 227 is preferably used in pulse-echo mode, although using multiple transducers (not shown) in pitch-catch mode is also possible. In general, higher frequencies are preferable if the sound is only traveling a short distance through blood in order to increase time resolution and narrow the acoustic beam. Lower frequencies are preferable for long paths to minimize attenuation.

The temperature of the sample may be measured directly by a temperature probe 90 such as a thyristor (as shown), or indirectly. Indirect means may include waiting for the sample to equilibrate with its environment and measuring the ambient or container temperature in lieu of the blood temperature. If the temperature of the blood is changing rapidly (because it has been freshly drawn for example) repeated ultrasonic measurements and/or temperature measurements allow the invention to infer a trend and predict what the final readings would be once the sample has reached thermal equilibrium with its surroundings. Since speed of sound in any apparatus or container changes with respect to temperature, the temperature of the container walls can be inferred by measuring the speed of sound through the walls. The temperature may also be controlled so that no temperature variations affect the measurement. The preferred embodiment employs measurement using a temperature sensing device 90 such as a thermistor. For example, thermistor 90 is included on the other side of sample chamber 22 for sensing the temperature of the blood sample in sampling device 12. Preferably, the thermistor 90 is mounted on the inner surface of the chamber so that it can measure the blood temperature by direct contact. If this presents cleaning or contamination problems, another preferable embodiment is to embed the thermistor directly behind the wall of the chamber 90. Measuring the temperature of the metal gap of sample chamber 22 also allows the device to compensate for thermal expansion. The transducers 227 and thermistor 90 are electrically connected to the circuit board internal to analyzer 10.

Once the analysis is complete, micro-pump 210 exerts a small amount of reverse pressure to force the blood out of the testing cell 25 and back into capillary tube 11. As the device 12 is removed from the analyzer 10, the sealing rings 26 again serve as a wiping mechanism, cleaning off the sensing surfaces 228. The danger of inadvertent exposure to the blood is eliminated by the sequential use of capillary action and pressure-differential to move the blood from containment, to sample chamber, and back, automatically upon insertion and withdrawal.

Figure 13:
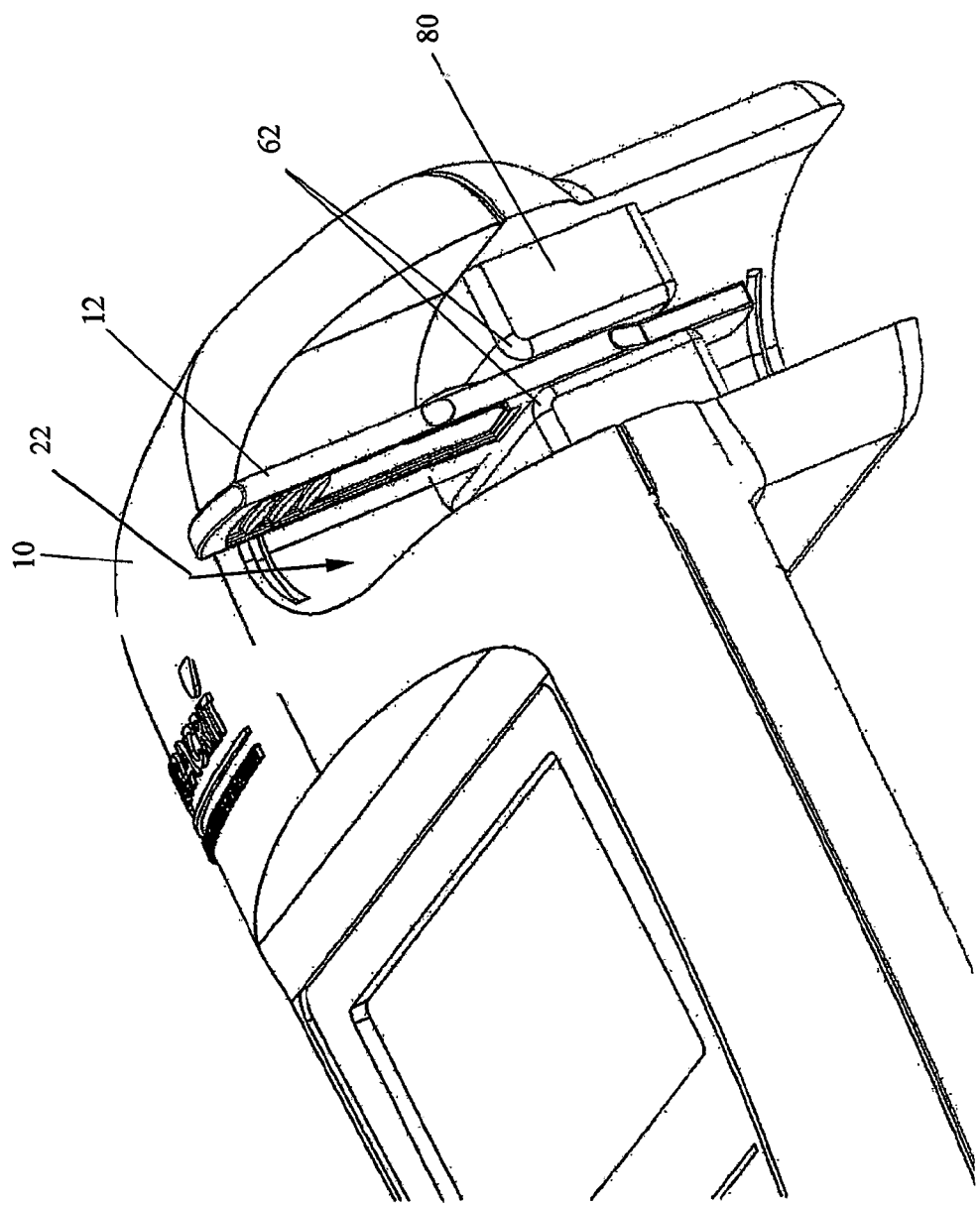
FIG. 13 is a side perspective view of the analyzer 10 with snap-in door 20 removed from its hinges to illustrate insertion of the sampling device 12 into sample chamber 80.

FIG. 13 is a side perspective view of the analyzer 10 with snap-in door 20 removed from its hinges to illustrate insertion of the sampling device 12 into sample chamber 22. The sample chamber 22 maintains precise alignment of the various components, especially the alignment between transducer(s) and the sampling device 12. The walls 62 of sample chamber 22 are formed of a material chosen for structural strength. Preferred sample chamber 22 materials include steel or brass. The chamber 22 is preferably manufactured to precisely known dimensions so that the sound path length (the distance between the two faces of the gap) is preferably known to +/−0.2%, more preferably to +/−0.05%. This is important because the device 10 calculates speed of sound from the measured time of flight based on this recorded distance. Alternatively, the gap size may be measured after manufacture as a calibration step and recorded in device memory. The sample chamber 22 is preferably sized relative to the sampling device 12 to contain a blood sample of <1 ml as described below, although anywhere from 0.01 to 1 mL will suffice. Correspondingly, the preferred distance between the faces of the gap is 0.5 mm-6 mm, preferably 3 mm.

Door 20 and Latching Mechanism 400

Figure 14:
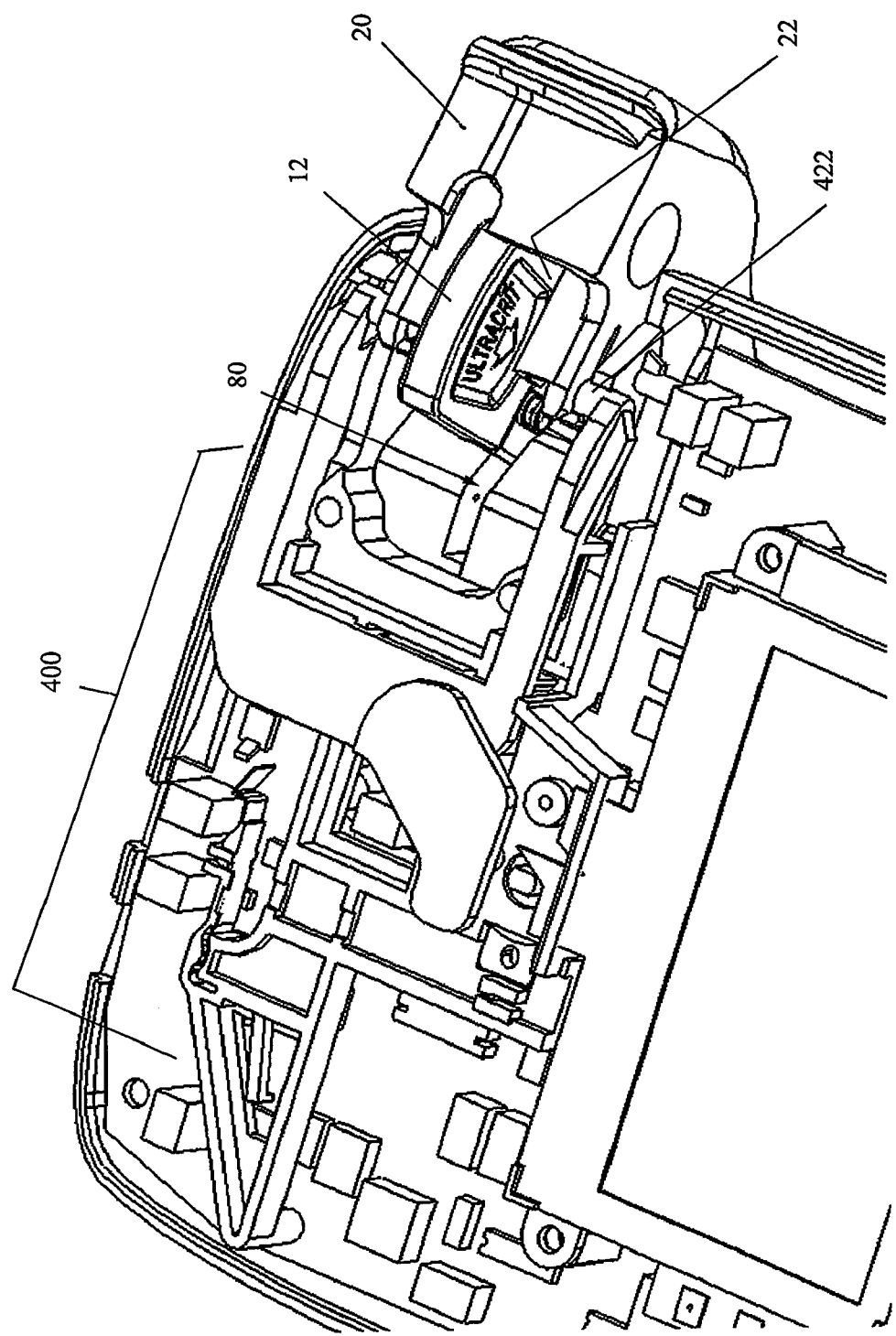
FIG. 14 is a top perspective view of the analyzer 10 with top housing section 30A removed to illustrate operation of the door 20 latching mechanism 400 during insertion of the sampling device 12 into sample chamber 80.
Figure 15:
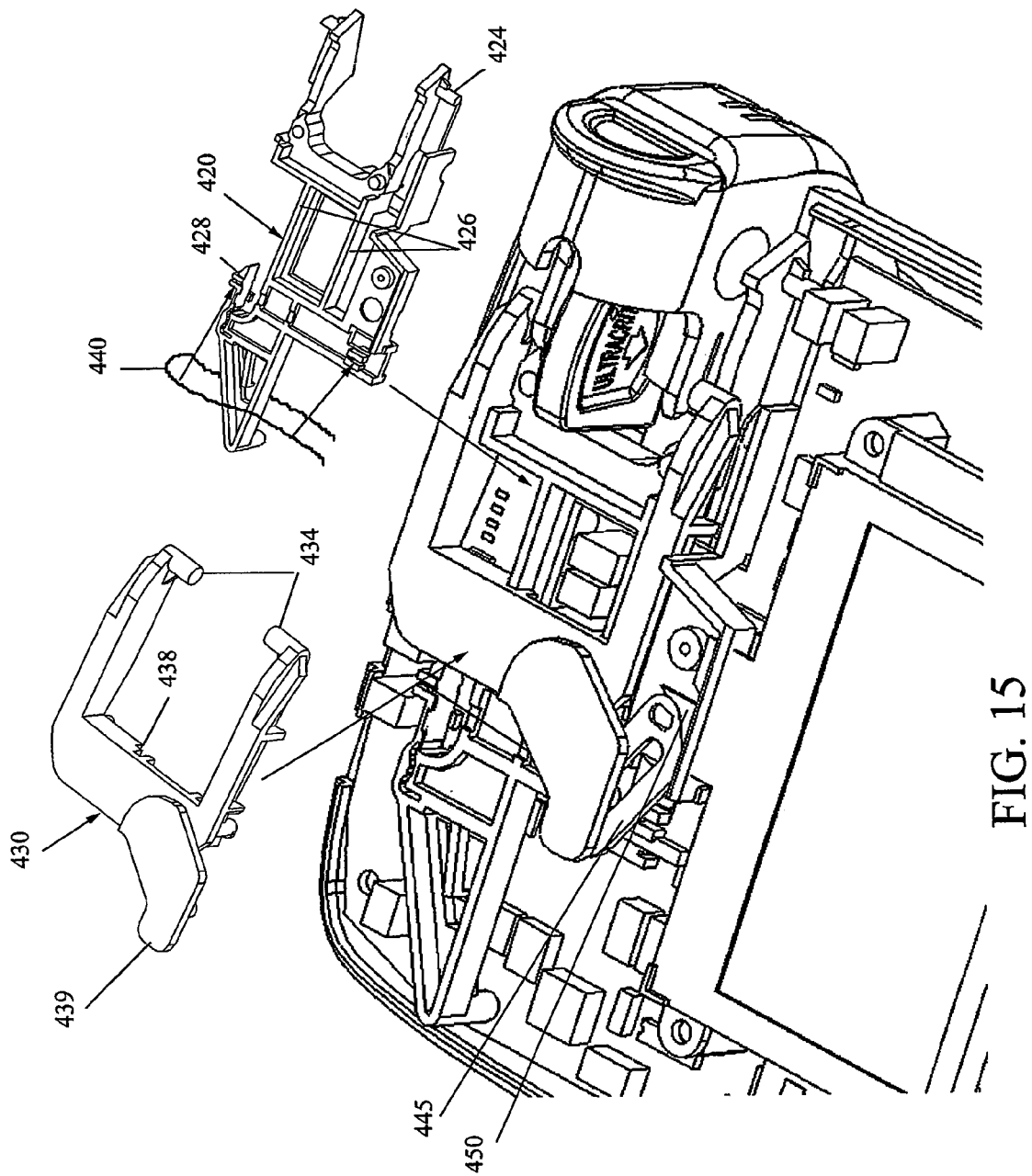
FIG. 15 is a similar view with door 20 closed and the primary components of the latching mechanism 400 exploded.

FIG. 14 is a top perspective view of the analyzer 10 with top housing section 30A removed to illustrate operation of the door 20 latching mechanism 400 during insertion of the sampling device 12 into sample chamber 22. The door 20 is shown open in FIG. 14. FIG. 15 is a similar view with door 20 closed and the primary components of the latching mechanism 400 exploded. With combined reference to FIGS. 14-15, the sample door 20 is side-oriented door with opposing hinges 422 that snap-into pivot joints in the lower housing 30B. The door 20 is formed with a contoured sample chamber 22 to guide slidable insertion of disposable 12. The sample door 20 then latches shut to precisely align and lock the disposable 20 in place in the sample chamber 22.

The latching mechanism 400 includes an assembly of interfitting parts that generally latch the door 20 closed as shown in FIG. 15, and automatically open the door 20 upon completion of the test procedure. The latching mechanism 400 includes a stationery undercarriage 420 with a set of pivot pins 424 for pivoting attachment of a lower end of door 20 as shown, and an articulating carriage 430 with a set of pivot pins 434 for pivoting attachment of an upper end of door 20. The articulating carriage 430 is adapted for sliding back-and-forth along rails 426 formed in the stationery carriage 420. Thus, when the articulating carriage 430 slides to the right, pins 434 push the upper end of door 20 rightward and open it. When the articulating carriage 430 slides to the left, pins 434 pull the upper end of door 20 leftward and close it. The latching mechanism 400 is biased open, and this is accomplished with one or more springs (not shown) stretched between the stationery undercarriage 420 and articulating carriage 430. As seen in FIG. 15, the stationery undercarriage 420 includes a resilient latch arm 428 that latches into a recess 438 formed on the underside of the articulating carriage 430. Thus, as the door 20 is closed (against the spring bias) and the articulating carriage 430 rides along the length of the stationery carriage 420, the door 20 arrives at a fully closed position, whereupon the resilient latch arm 428 latches into recess 438 and locks the door 20 shut. An automatic release mechanism is also provided for releasing the door 20 and allowing it to spring open after testing. This may be economically accomplished with a length of shape memory alloy 440 (nickel-titanium, Nitinol®) wound around the resilient latch arm 428 (guide blocks may be provided as shown) and connected at its distal ends to the circuit board. This way, when the testing is complete an electrical current is applied through the length of shape memory alloy 440 causing it to contract, pulling the latch arm 428 inward, disengaging it from recess 438 and freeing articulating carriage 430, thereby allowing the spring-biased door 20 to pop open for removal of disposable 12. One skilled in the art will understand that alternative automatic releasing mechanisms are possible, such as solenoid releases. The motion of the door 20 (the relative motion of articulating carriage 430 and stationery carriage 420) is governed by a damping mechanism including a lever arm 439 protruding from the articulating carriage 430. The lever arm 439 is pivotably mounted along a reduction arm 445, which in turn is mounted to a stationery conventional damping hinge 450. Thus, as the door 20 is closed and the articulating carriage 430 rides leftward along the length of the stationery carriage 420, the lever arm 439 rides backward along reduction arm 445 and turns it against the bias of damping hinge 450. Conversely, when the door 20 is released it swings open and the articulating carriage 430 rides rightward along the length of the stationery carriage 420, the lever arm 439 rides forward along reduction arm 445 thereby decreasing its leverage, and simultaneously turns reduction arm 445 against the bias of damping hinge 450. This imparts a damping action, stronger during closure, to avoid jerky movement and spillage or spraying of blood.

The above-described door 20 and latching mechanism provide a number of distinct advantages. Most importantly, it facilitates a precise alignment of the disposable device 12 in sample chamber 22 and the positive latching avoids inadvertent partial-insertion. The pocketed door 20 allows loose and easier insertion and removal of sampling device 12, enabling quicker insertion and reduced time for the blood sample to clot. The positive latching upon closure prevents opening during the test when the blood sample is exposed, thereby minimizing the risk of spilled or splashed blood. Additionally, the automatic opening of door 20 provides an unmistakable indication that the test is complete, allowing quick removal of the disposable device 12 and keeping both door 20 and sample chamber 22 clean and free of blood. These features make the device much more user-friendly and safe, less error-prone despite unskilled users. Moreover, the door 20 can be easily unsnapped from its hinges for easy cleaning of the door 20 and sample chamber 22.

Electronics Subsystem 200

The electronics subsystem 200 contained on the internal circuit board is responsible for controlling the four functions shown in FIG. 5, namely, generating a precisely controlled electric signal at step 12, sending and receiving the ultrasonic waves at step 110, analyzing the received waves at step 120, sampling the temperature at step 130, and computing the clinically-relevant results at step 140. Thus, the electronics generally includes means for exciting the transducer(s) 82, signal capture there from, and analysis. These various means may be provided as separate devices, or they may be integrated together as a single component.

The electronics subsystem also controls he micro-pump 90, and the latching mechanism 400.

Figure 16:
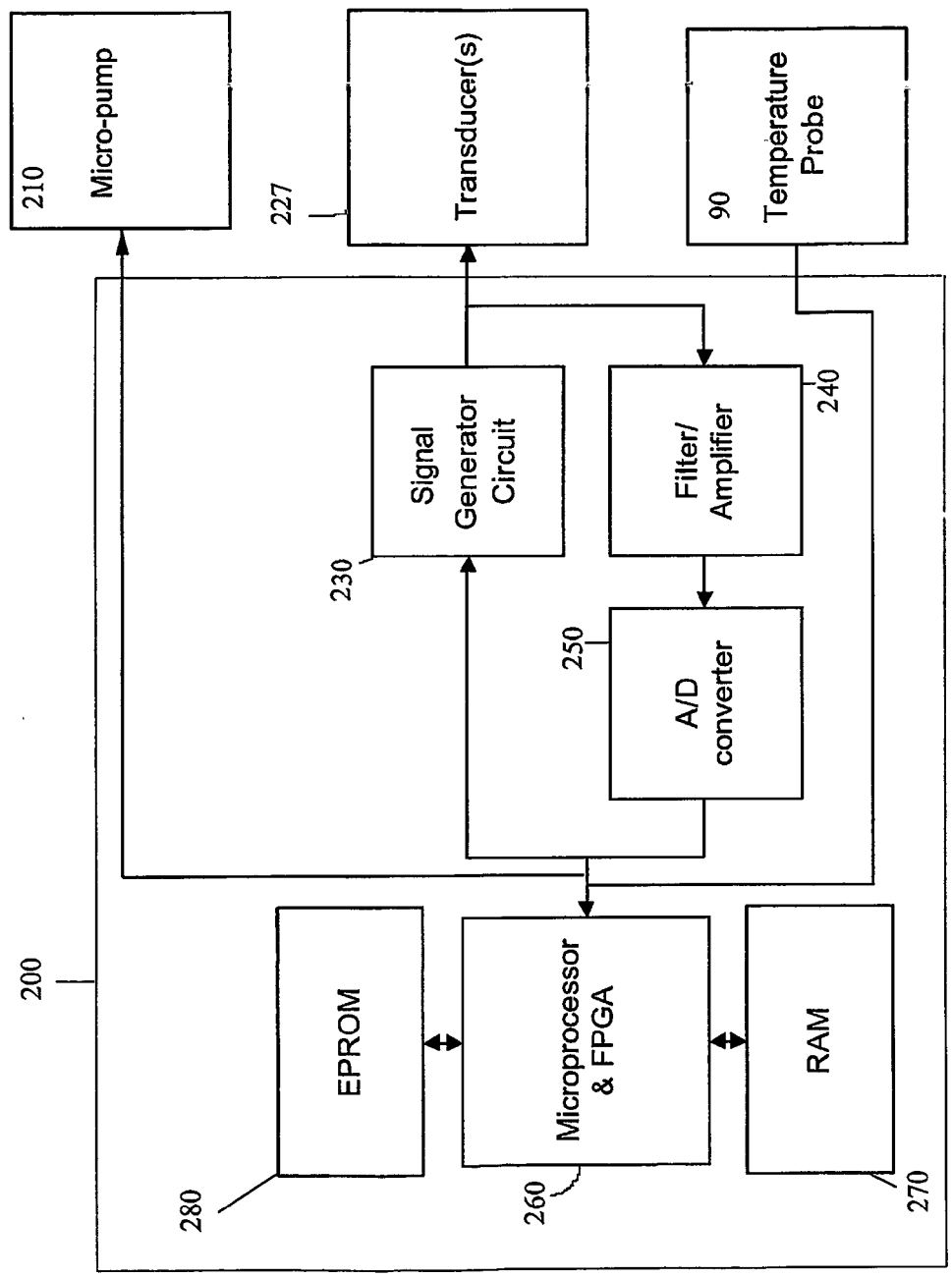
FIG. 16 is a block diagram of the electronics subsystem 100 adapted to carry out the steps illustrated in FIG. 5.

FIG. 16 is a block diagram of the electronics subsystem 200 preferably implemented to carry out the steps that were illustrated in FIG. 5. The sending stage preferably includes a signal generator circuit 230 which comprises a conventional programmable signal generator, known signal conditioning components as necessary to amplify, filter, and/or reduce noise, and a power amplifier, with output coupled to transducers 82. The signal generator circuit 230 generates a simple electronic signal of sufficient duration and amplitude to operate the transducers. The frequency of the signal is appropriate for the selected transducer 227, and is preferably from 0.25 to 3 cycles in length. The amplitude of signal should be as high as possible without exceeding the transducers' ratings. Another amplifier circuit may be needed to maximize the signal-to-noise ratio. The signal generator circuit 230 functions to generate a gated sinusoid, square pulse, spike with exponential delay or other function. The signal normally would have a center frequency matched to the center frequency of the transducer 227 in use to maximize the amount of energy delivered to the sample. For frequency sweeps, the frequency range is preferably chosen to lie within the usable bandwidth of the transducer 227. The signal generator circuit 230 will preferably generate an electronic pulse to operate the transducer 227 in pitch-catch or pulse-echo mode. The frequency of the signal may be from 1 to 50 Mhz, preferably at least 6 Mhz, and 10 Mhz is currently most suitable, depending on the type of measurement being made and the size of the sample chamber. Higher frequencies should be chosen if the sound is only traveling a short distance through blood in order to increase time resolution, reduce sensitivity to coherent noise, reduce the beam angle, or to achieve wavelengths proximate in length to a red blood cell diameter. Lower frequencies should be chosen for long paths to minimize attenuation. The ultrasonic signal returned from the sample causes the transducer 227 to generate an electrical signal that is passed along to the receiving stage. The receiving stage preferably includes signal conditioning and an amplifier 240, a digitizer (A/D Converter) 250, and a means for collecting and analyzing data, such as a microprocessor 260 or microcontroller, and RAM 270 for storing the data (or alternatively, magnetic storage or CD). The control sequence and analysis software for testing, the micro-pump 90, latching mechanism 400, and diagnostics (to be described) is stored in EEPROM 222.

All of device control, signal processing and detection logic is accomplished by the on-board processor 260, inclusive of signal measurements and calculations including transit times and amplitude based on the digitized signal from the by the A/D Converter 250. The signal processing algorithms preferably include one or more of the following: noise filtering, averaging, and automatic gain control, which are understood by one of ordinary skill in ultrasonics or electrical engineering, and which are not particularly limited. Detection logic preferably includes cross-correlation, zero crossing detection, or other timing techniques known to those skilled in the art. Device control is also performed by processor 260.

The amplifier 240 is needed to bring the signal amplitude up to a level that can be readily captured by a digitizer 250 and/or analyzed by analog electronics. Therefore, the amplifier should be chosen to have the needed gain. The amplifier 240 should also be chosen to have the appropriate bandwidth for the planned measurements. The amplifier 240 may also include one or more filters built-in. The filters are used to eliminate noise that lies outside the frequency band being measured. Suitable filters include active and passive filters, RC filters.

Referring back to FIG. 4, a communication port 60, for example, a universal serial bus or other standard computer communication port is electrically coupled through a USART (not shown) or other communication IC to processor 260, the communication port 60 being panel-mounted at the rear of housing 30 to allow a user to connect a remote computer to the internal circuit board for remote diagnostics, data downloading, and other purposes. This allows the analyzer 10 to communicate with other medical equipment, a hospital device network, or both.

Software

Hematocrit is defined as the volume fraction of red blood cells in a sample of blood. The speed of sound in blood is a direct function of the hematocrit (HCT) and hemoglobin in the blood (HGB). This relationship arises because red blood cells and hemoglobin have different material compositions from the surrounding plasma and therefore different speeds of sound. The speed of sound of whole blood is approximately the weighted average of the speeds of sounds of its components. In other words, the higher the concentration of red blood cells, the more the speed of sound of the blood will approximate that of red blood cells instead of plasma. Because red blood cells make up nearly 50% of the blood volume, HCT and HGB are by far the strongest variables affecting the speed of sound in a blood sample. Variations of other blood components (white blood cells, platelets, extracellular proteins) may change the speed of sound slightly and limit the accuracy of the invention, but their influence is small enough that it has not been materially significant in experiments to date.

Since the majority of the hemoglobin is in the red blood cells under normal physiological conditions, the HGB and HCT results typically provide equivalent information to the physician. They both indicate the oxygen-carrying capacity of the blood. The following generalized functions demonstrate the physical dependence of speed of sound on HCT and temperature:

$$Cf = g(HCT, T)$$

$$Cf = f(HGB, T)$$

Where:

Cf is the speed of sound in blood, HGB is concentration of hemoglobin, HCT is hematocrit, T is temperature, and f and g are functions that must be determined empirically.

Because speed of sound is a function of HGB and HCT, one can measure speed of sound and apply it as an indication of the HGB and/or HCT by inverting the calculation.

The preferable way to calculate speed of sound is by measuring the time of flight of one or more short ultrasonic pulses over a known distance.

$$Cf = d/t$$

Where:

Cf is the speed of sound, d is the distance the sound travels through the sample, and t is the measured time it takes for the sound to travel that distance.

Figure 17:
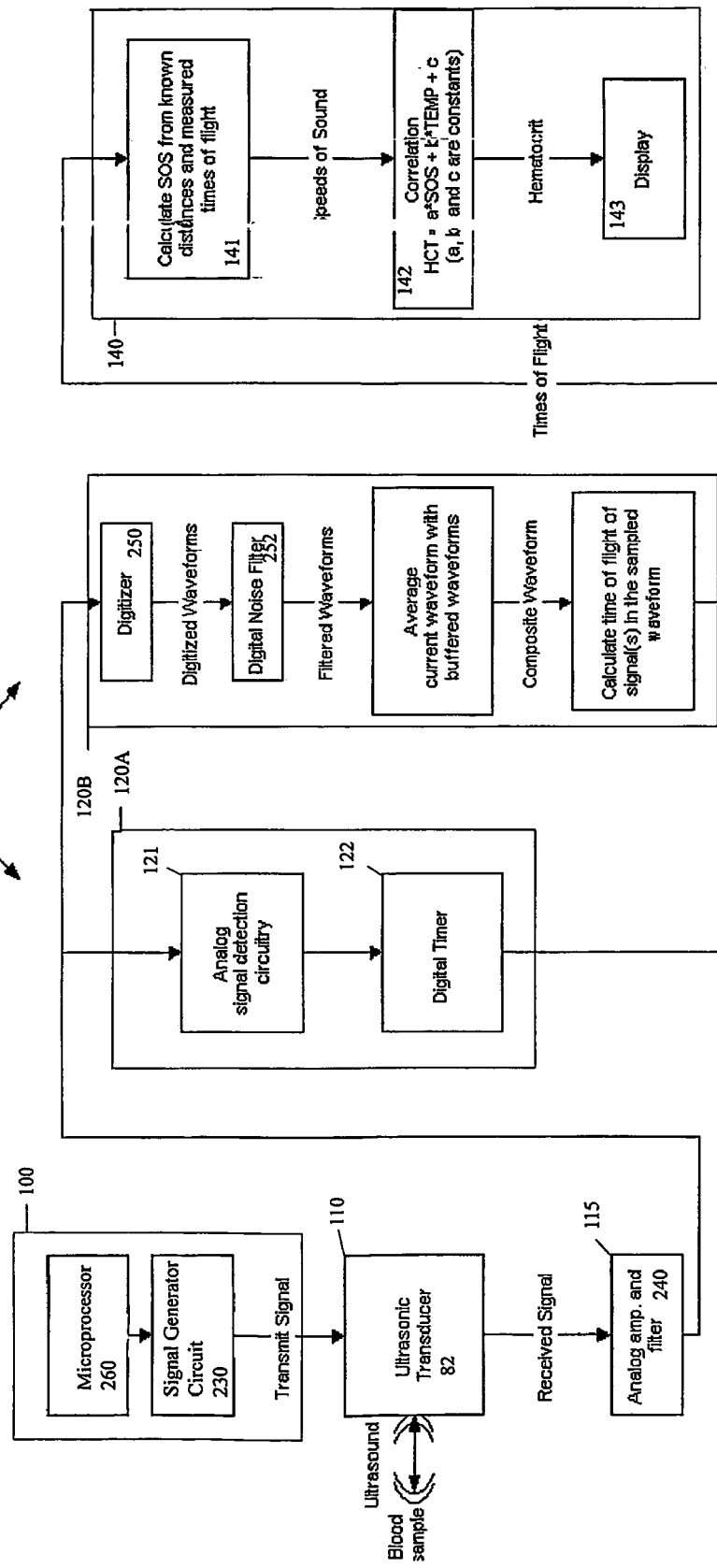
FIG. 17 is a flowchart illustrating the software steps for implementing the above-described measurement method steps illustrated in FIG. 5.

FIG. 17 is a flowchart illustrating exemplary software steps for implementing the above-described measurement method, using either of two alternative speed of sound measurement techniques. With both techniques the method begins with a signal generation step 12 (see also FIG. 5) wherein microprocessor and/or FPGA 260 (FIG. 16) triggers the signal generator circuit 230, which creates the pulse waveform. Presently, a series of pulses are emitted over a specified test interval, although this may be varied from a single pulse to any variety of pulse trains as a matter of design choice. At step 110 the signal generator outputs the pulse waveform to the ultrasonic transducer(s) 82 which transmit the pulse waveform through the blood sample, and then receives returning pulses that are reflected from the far wall of the sample chamber 22. At step 115 a conditioning step is performed by which the received pulses are filtered and amplified by filter/amplifier 240.

The device then performs a signal analysis step 120 which, as shown by the alternate branches 120A and 120B, may be an analog signal analysis or digital signal analysis, respectively. The analog signal analysis 120A entails signal sensing of the received signals by an analog signal detection circuit 121, and timing receipt of the signals using a digital timer 122 to determine the time t (the measured time it takes for the sound to travel the predetermined distance d through the blood sample). Alternatively, the digital signal analysis approach 120B entails digitizing the received signals at A/D converter or digitizer 250, filtering the digitized signals at digital noise filter 252, and feeding the information back to microprocessor and/or FPGA 260.

In both cases, the microprocessor 260 adds the flexibility range-gating the received and digitized signals, and/or of compiling an average of received signals, in both cases improving the accuracy of the device. Range-gating helps to discern the most relevant reflections, given any individual output pulse may engender multiple reflections not all of which are relevant. Only reflected signals received during pre-determined time intervals are considered during the signal analysis. Thus, for any given output pulse, microprocessor 260 can be programmed to expect a reflected pulse emanating from the near surface of the blood sample during a predetermined interval, and from the far wall of the chamber during a second predetermined interval. The two reflected pulses that selectively fall within these two intervals can be isolated and subtracted to determine time of flight of sound through the blood sample, thereby excluding variables such as the time of flight through the window 84 or delays in the electronics 200. Moreover, where multiple output pulses are emitted during a test interval, the processor 260 can maintain an average time of flight for the multiple samples. The average can be a rolling average (averaged over successive groups, say ten or so output pulses), or a cumulative average of all output pulses within a given test interval. Again, range-gating and pulse-averaging helps to increase the accuracy and consistency of the device.

Of course, there are many acceptable variations on the foregoing techniques, such as averaging sampled waveforms with prior buffered waveforms and computing a composite averaged waveform from which processor 260 calculates the time of flight of the signal(s) in the sampled waveform. All are considered to be within the scope and spirit of the present device.

For both of the above-described approaches (digital and analog) 120A & 120B, the method proceeds to step 140 which entails a computation of clinical results. More specifically, at substep 141 processor 260 calculates the speed of sound (SOS) in the sampled waveform based on time of flight of the signal(s). Given the speed of sound, the processor 260 is then able at substep 142 to derive hematocrit (HCT) from the speed of sound and temperature measurement based on the correlation HCT=a*SOS+b*TEMP+c, (where a, b, and c are empirically-determined constants). Exemplary coefficients have been empirically determined to be as follows, albeit these coefficients are typically derived empirically for each system to account for system biases and so the present calculations should not be taken to be limited to these particular coefficients.

a=1.01179
b=−1.98782
c=−1489.70

It is also noteworthy that the foregoing assume linear equations, but higher order calculations exist, may easily be implemented in the present system, and are considered to be within the scope and spirit of the present invention. The linear form has been found to be simple and accurate for purposes of the presently-preferred embodiment.

It is also implicit in the foregoing that temperature affects speed of sound so the results are temperature-dependent and must be adjusted to account for temperature variations. This is accomplished using one or more temperature measurements from thermistor 90. Furthermore, depending on the materials chosen for the invention, it may need to account for temperature affects on the sizes and shapes of its component parts.

Given a computation of clinical results from step 140, at substep 143 the HCT clinical measurement is displayed at display 40.

Likewise, given the speed of sound and temperature, the hemoglobin concentration can be determined based on the like correlation HGB=d*SOS+e*TEMP+f (where d, e, and f are empirically determined constants) and the hemoglobin concentration HGB clinical measurement can likewise be displayed.

It is noteworthy that the device 10 is capable of employing other known techniques for measuring speed of sound, and these are also suitable for use in the present invention. Moreover, other measurable ultrasonic characteristics (other than the speed of sound) are suitable for use in correlating HCT or HGB such as measuring attenuation and backscatter of the ultrasonic signals. Again, temperature affects attenuation coefficient and backscatter so the results are temperature dependant and must be adjusted to account for temperature variations. This is accomplished using one or more temperature measurements from thermistor 90.

General Use and Operation of Device 10

In the embodiment described above, the user draws a drop of blood via a finger or heel stick and collects it in the sampling device 12. The sampling device 12 is placed into the analyzer 10 in door 20, the door 20 is closed and latched, and the device will automatically display the hematocrit and/or the hemoglobin concentration. Inserting the sampling device 12 requires very little skill, experience or instruction as it fits into the device only in the correct orientation. The control software run by analyzer 10 performs the following functions behind the scenes and guides the user via display 40.

A. Power up: power up shall boot up the analyzer 10, run electronic self-checks and determine if repair is needed. After power up, the display indicates that the analyzer 10 is ready to accept and test additional samples. The control software may perform self tests between donor tests to detect the need for cleaning.

B. After testing, the results are displayed at display 40.

C. Release: the analyzer 10 automatically ejects the sample via latching mechanism 400 when testing is complete (to avoid coagulation and drying in the test chamber) and also prompts the user at display 40 to "REMOVE SAMPLE." If desired, the sampling device 12 may be automatically locked into the analyzer 10 during testing.

Diagnostics

In addition to the simple electronic self-checks described above, the analyzer 10 facilitates a user-assisted self test of the overall accuracy of the device. This employs a special diagnostic disposable device filled with a calibrated liquid or "QC fluid" (this can be any fluid preferably with ultrasonic properties similar to blood, saline solution being an acceptable example).

Figure 18:
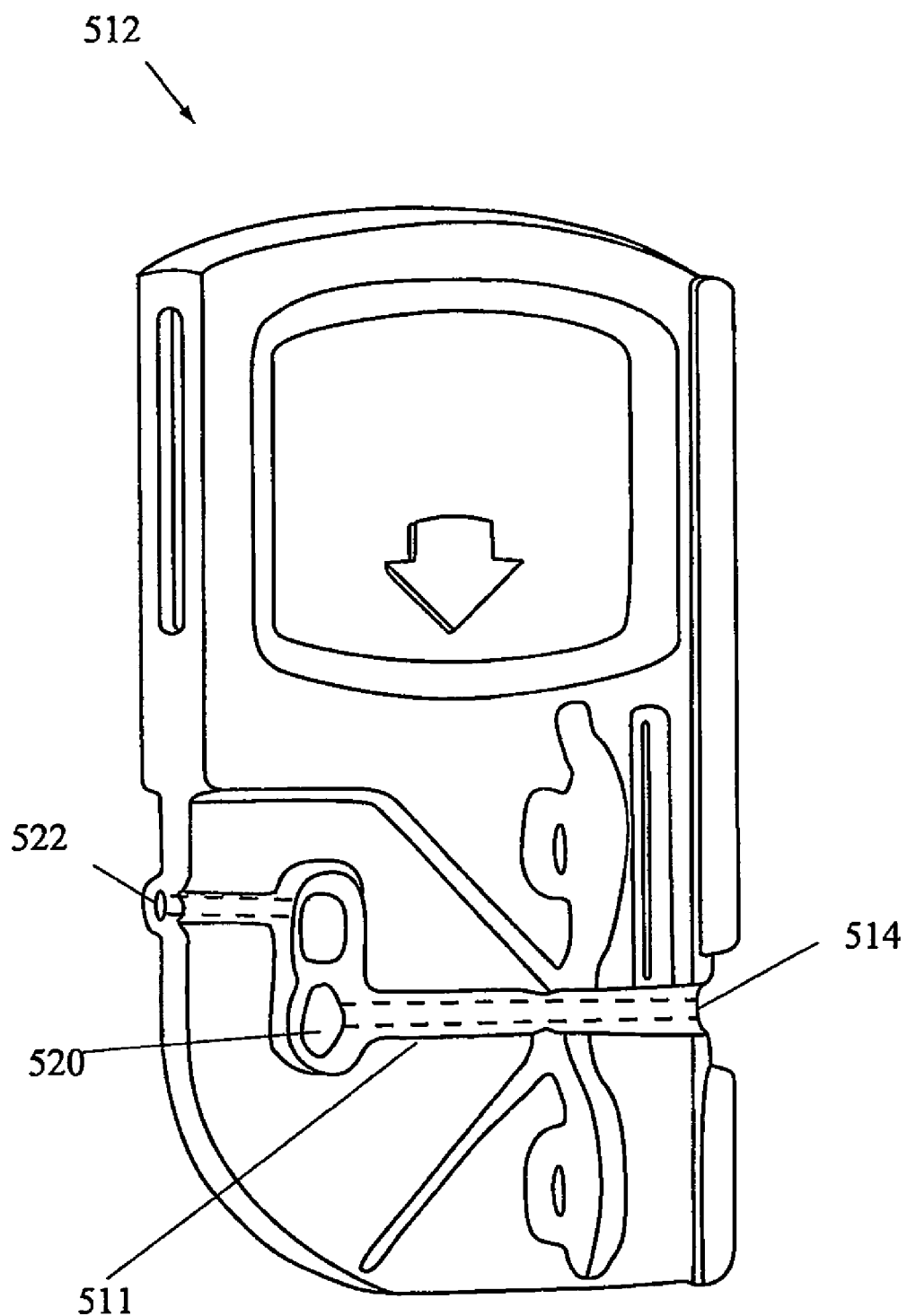
FIG. 18 is a front view of a calibrated sampling device 512.

FIG. 18 is a front view of a calibrated, sampling device 512 that again generally comprises an elongate and relatively thin rubber supporting frame configured and formed as the sampling device 12 described above with reference to FIGS. 6-9. However, rather than an open capillary input, calibrated sampling device 512 includes a dropper port 514 connected to a like testing region 20 and actuator region 30. The dropper port 514 comprises an entrance aperture for placement of approximately 50 micro-liters of sample QC fluid. The QC fluid is inducted by closed capillary tube 511 to testing region 520. It is noteworthy that the capillary tube 511 connecting to testing region 520 is horizontally-disposed for the calibrated sampling device 512, rather than vertically as with the actual sampling device 12. Whereas a vertical orientation is necessary to reduce settling of red blood cells, this problem is not faced with QC fluids such as saline. The horizontal orientation ensures a more uniform distribution of the calibration sample of QC fluid. The capillary tube 511 continues past the testing region 520 to a pump orifice 522 as in the blood sampling disposable 12. The calibrated sampling device 512 is pre-marked with calibration values representing the expected speed of sound (SOS) through the QC fluid sample based on time of flight of the signal(s). Given the same form of clinical computation described above with regard to a blood sample, the calibrated sampling device 512 allows a dependable user-self test using a QC fluid sample with calibration results conveniently displayed at display 40. The user merely needs to confirm that the calibration results match those pre-printed on the calibrated sampling device 512.

INDUSTRIAL APPLICABILITY

Blood testing is typically done with syringes and laboratory blood analyzers. However, more recent advances are resulting in portable and more convenient (less intrusive) products. There are few portable blood analyzers appearing on the market that generally accept a test strip (coated with a blood sample and reagent) or the like. However, these are extremely messy and do not safeguard the transfer of the blood sample from patient to analyzer in the least respect. The present invention is a blood analyzer suitable for portable or handheld applications, and also for tabletop or permanent installations. The system is fast and suitable for accuracies to as little as 1% as verified by international reference standards. In addition, the invention is suitable for minimally-invasive measurements (using the blood sampling device to place a very small blood sample in the measurement chamber). The system attributes as described above are reflective of the very first point of care HCT and/or HGB measurement device with accuracy comparable to larger CBC lab equipment. This provides a significant improvement over conventional devices in each of the following areas:

Portability—the components in the device are small, durable, and lightweight. Target weight is less than 10 pounds, which is less than one third of the weight of automated cell counters.

Speed—A single ultrasonic pulse and measure cycle takes fractions of a second and firmware signal analysis would allow nearly instantaneous results. Target cycle time is less than 60 seconds, which is a 90% improvement over the minimum 10 minutes required for processing by a blood lab. With the present invention, accurate hematocrit and hemoglobin concentration measurements are provided with a turn-around time of just one minute, more than a 90% reduction in time from sample to results. Simple and accurate HCT and HGB measurements are thus available without the wait.

Accuracy—two-times better than existing portable devices . . . better than 2%.

The present invention is useful in both civilian and military emergency medical environments, and can be implemented as a small, lightweight, self-contained, and durable device that may be readily carried to the scene of an emergency. It serves the private practice physician as it provides an alternative to contract blood analysis laboratories when results are needed immediately with high accuracy. The speed and accuracy provide physicians with information that they can use during the same visit, saving time on follow-up visits and telephone calls. It can also serve blood banks by accurately screening donors for anemia.

Having now fully described this invention, it will be apparent to one of ordinary skill in the art that many changes and modifications can be made thereto without departing from the spirit or scope of the invention as set forth herein.

We claim:

1. A system for determining hematocrit or hemoglobin concentration of blood, comprising: a sampling device for collecting a blood sample; and an analyzer adapted for insertion of said sampling device and for measuring and displaying hematocrit or hemoglobin concentration of said blood sample, said analyzer further comprising, a signal generator for generating an electronic signal, at least one transducer coupled to said signal generator for converting the electronic signal to an ultrasonic signal, said at least one transducer being oriented toward an aperture in said sampling device for emitting the ultrasonic signal into the blood sample while still inside said sampling device, and for receiving ultrasonic reflections from said blood sample, a receiver for measuring a physical parameter from said ultrasonic reflections, and a processor for calculating any hematocrit or hemoglobin in said blood sample from said measured physical parameter.

2. The apparatus for determining hematocrit or hemoglobin concentration of blood according to claim 1, wherein said aperture defines a test cell in said sampling device, and said at least one transducer covers said aperture when said sampling device is inserted in said analyzer.

3. The apparatus for determining hematocrit or hemoglobin concentration of blood according to claim 2, wherein said sampling device includes a capillary channel for inducting a blood sample.

4. The apparatus for determining hematocrit or hemoglobin concentration of blood according to claim 3, wherein said analyzer comprises a micro-pump for pumping said blood sample from said capillary channel into said test cell.

5. The apparatus for determining hematocrit or hemoglobin concentration of blood according to claim 1, wherein said analyzer comprises a pivoting door having a pocket for insertion of said sampling device, and for pivoting said sampling device into a test chamber in said analyzer.

6. The apparatus for determining hematocrit or hemoglobin concentration of blood according to claim 5, wherein said door is spring-biased to an open position.

7. The apparatus for determining hematocrit or hemoglobin concentration of blood according to claim 6, further comprising a latching mechanism for latching said pivoting door shut.

8. The apparatus for determining hematocrit or hemoglobin concentration of blood according to claim 7, wherein said latching mechanism comprises a stationary undercarriage and a slidable carriage mounted on said undercarriage.

9. The apparatus for determining hematocrit or hemoglobin concentration of blood according to claim 7, further comprising an electronically-controlled unlatching mechanism for unlatching said door.

10. The apparatus for determining hematocrit or hemoglobin concentration of blood according to claim 9, wherein said unlatching mechanism includes a shape memory alloy.

11. A method of self-testing an analyzer for determining hematocrit or hemoglobin concentration of blood as described in claim 1, comprising the steps of: placing a calibrated test fluid in a sampling device and recording an expected physical parameter directly on said sampling device; inserting said sampling device into said analyzer with said test fluid contained therein; measuring and displaying a physical parameter from ultrasonic reflections therein; and calculating and displaying an actual physical parameter from said calibrated test fluid at said analyzer for comparison by a user to the expected physical parameter recorded on said sampling device.

12. A disposable blood sampling device for use in conjunction with an analyzer as described in claim 1, comprising a capillary tube with an inlet aperture for drawing a test fluid into said sampling device, said capillary tube being substantially vertically-oriented when inserted into said analyzer, and a testing cell in fluid communication with said capillary tube.

13. A calibration sampling device for use in conjunction with an analyzer as described in claim 1, comprising a capillary tube for drawing a test fluid into said sampling device, said capillary tube being horizontally oriented when inserted into said analyzer, and a testing cell in fluid communication with said capillary tube.

14. An apparatus for determining hematocrit or hemoglobin concentration of blood, comprising: a sampling device for acquiring a blood sample, said sampling device comprising a body having a finger-grip at one end and an opposing functional end, said functional end further including a collecting region including an entrance aperture through which fluid enters the device by capillary action and flows into said collecting region, a testing region in fluid communication with said collecting region for containing said fluid during testing inside an analysis unit, and a pumping region in fluid communication with said testing region for introducing a pressure-differential and thereby inducting said fluid from said collecting region into said testing region for testing; and said analysis unit comprising a sample port for insertion of said sampling device, a signal generator for generating electronic signals, at least one transducer coupled to said pulse generator and oriented toward the testing region on said sampling device for emitting ultrasonic signals through the blood sample while in said sampling device in accordance with said electronic signals, and for receiving ultrasonic reflections from said blood sample, a temperature probe for measuring temperature of said blood sample, a receiver for measuring a physical parameter from said ultrasonic reflections, and a processor for calculating any hematocrit or hemoglobin in said blood sample from said measured physical parameter.

15. The fluid sample collection device according to claim 14, wherein said pumping region comprises a bulb for introducing said pressure-differential.

16. The fluid sample collection device according to claim 15, wherein said bulb is operated by insertion of said collection device into said analysis unit and squeezing thereof during insertion.

17. The fluid sample collection device according to claim 15, wherein said bulb is operated by squeezing via an actuator in said analysis unit.

18. The fluid sample collection device according to claim 14, wherein said pumping region comprises an orifice for coupling a pump in said analysis unit to said testing region for introducing said pressure-differential.

19. The fluid sample collection device according to claim 18, wherein said testing region comprises an open-ended chamber that is sealed by insertion between sensor walls of said analysis unit.

20. A blood analysis device, comprising: a disposable blood sampling device having means for collecting a fluid sample by capillary action, and means for transporting said fluid to a testing cell by pressure-differential for testing by an analysis unit; and said analysis unit into which said disposable fluid sampling device may be inserted for measuring time of flight of ultrasound through the blood sample whilst still in said disposable sampling device and for calculating hematocrit or hemoglobin concentration in said blood sample from measuring said time of flight of ultrasound.

* * * * *